US006699499B1

(12) United States Patent
Aneja

(10) Patent No.: US 6,699,499 B1
(45) Date of Patent: *Mar. 2, 2004

(54) AMPHIPHILIC MATERIALS AND LIPOSOME FORMULATIONS THEREOF

(75) Inventor: Rajindra Aneja, Ithaca, NY (US)

(73) Assignee: Nutrimed Biotech, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/879,368

(22) Filed: Jun. 11, 2001

Related U.S. Application Data

(62) Division of application No. 08/912,978, filed on Aug. 13, 1997, now Pat. No. 6,284,267.
(60) Provisional application No. 60/024,382, filed on Aug. 14, 1996.

(51) Int. Cl.[7] .............................................. A61K 9/127
(52) U.S. Cl. .................. 424/450; 424/1.21; 424/9.321; 424/9.51; 424/417; 424/94.3; 428/402.2; 554/79; 554/80; 554/103; 554/227
(58) Field of Search ................ 424/450, 1.21, 424/9.321, 9.51, 417, 94.3; 428/402.2; 436/829; 554/76, 80, 103, 227

(56) References Cited

U.S. PATENT DOCUMENTS

| 4,772,471 A | 9/1988 | Vanlerberghe et al. ...... 424/450 |
| 4,830,857 A | 5/1989 | Handjani et al. ............ 424/450 |
| 4,837,028 A | 6/1989 | Allen ......................... 424/450 |
| 4,920,016 A | 4/1990 | Allen et al. .................. 424/450 |
| 5,013,556 A | 5/1991 | Woodle et al. ............... 424/450 |
| 5,153,000 A | 10/1992 | Chikawa et al. ............. 424/450 |
| 5,225,212 A | 7/1993 | Martin et al. ................ 424/450 |
| 5,395,619 A | 3/1995 | Zalipsky et al. ............. 424/450 |

| 6,284,267 B1 | * | 9/2001 | Aneja |

FOREIGN PATENT DOCUMENTS

EP  0370491  4/1995

OTHER PUBLICATIONS

Allen and Chonn, "Large unilamellar liposomes with low uptake into the reticuloendothelial system," *FEBS Lett.*, 223(1):42–46, 1987.
Allen, Hansen, Martin, Redemann, Yau–Young, "Liposomes containing synthetic lipid derivatives of poly(ethylene glycol) show prolonged circulation half–lives in vivo," *Biochim. Biophys. Acta*, 1066:29–36, 1991.
Amselem, Cohen, Barenholz, "In vitro tests to predict in vivo performance of liposomal dosage forms," *Chem. Phys. Lipids*, 64:219–237, 1993.
Aneja, "Structural and stereochemical purity of glycerophospholipids," *Biochem. Soc. Trans.*, 2:38–41:1974.

(List continued on next page.)

Primary Examiner—Gollamudi S. Kishore
(74) Attorney, Agent, or Firm—Williams, Morgan and Amerson

(57) ABSTRACT

Disclosed is a new structural class of amphiphilic molecules which incorporate a hydrophilic material or polymer attached, at spatially distinct sites, to at least two hydrophobic residues. Certain of the amphiphilic molecules comprise a plurality of hydrophobic moieties. All such amphiphilic molecules have a common structural motif and, in contact with water, display surface activity and self-assemble into multimolecular aggregates and liquid crystalline phases. Also disclosed are enhanced stability liposomes that incorporate such amphiphilic molecules via unique interactions, and methods of using such formulations in a variety of applications including drug delivery, nutrition, biodiagnostics, cosmetics, blood products and related applications.

45 Claims, 10 Drawing Sheets

OTHER PUBLICATIONS

Aneja, "Novel biomolecular approaches to steric stabilization of liposomes: materials and organization," An American Chemical Society Symposium, ACS Annual Meeting, Sep. 8–11, Las Vegas, NV, 1977.

Aneja, "Novel biomaterials for optimizing liposomal drug delivery," *213th ACS National Meetingof the American Chemical Society*, San Francisco, California, USA, *Abstracts of Papers American Chemical Society*, 213:(1–3), Abstract BIOT–003, Apr. 13–17, 1997.

Aneja, Chadha, Davies, "A general synthesis of glycerophospholipids," *Biochim. Biophys. Acta*, 218:102–111, 1970.

Aneja and Davies, "The synthesis of a spin–labelled glycero–phospholipid," *Chem. Phys. Lipids*, 4:60–71, 1970.

Bahr, Deppe, Karas, Hillenkamp, "Mass spectrometry of synthetic polymers by UV–matrix–assisted laser desorption/ionization," *Anal. Chem.*, 64:2866–2869, 1992.

Balch, Morris, Brooks, Sleight, "The Use of N–(7–nitrobenz–2–oxa–1,3–diazole–4–yl)–labeled lipids in determining transmembrane lipid distribution," *Chem. Phys. Lipids*, 70:205–212, 1994.

Banagham and Horne, "Negative staining of phospholipids and their structural modification by surface–active agents as observed in the electron microscope," *J. Mol. Biol.*, 8:660–668, 1964.

Bangham, Standish, Watkins, "Diffusion of univalent ions across the lamellae of swollen phospholipids," *J. Mol. Biol.*, 13:238–252, 1965.

Bartlett, "Phosphorus assay in column chromatography," *J. Biol. Chem.*, 234(3):466–468, Mar. 1959.

Beauchamp, Gonias, Menapace, Pizzo, "A new procedure for the synthesis of polyethylene glycol–protein adducts; effects on function, receptor recognition, and clearance of superoxide dismutase, lactoferrin, and $\alpha_2$–macroglobulin," *Anal. Biochem.*, 131:25–33, 1983.

Blume and Cevc, "Liposomes for the sustained drug release in vivo," *Biochim. Biophys. Acta*, 1029:91–97, 1990.

Caffrey, "Kinetics and mechanism of the lamellar gel/lamellar liquid–crystal and lamellar/inverted hexagonal phase transition in phosphatidylethanolamine: A real–time x–ray diffreaction study using synchrotron radiation," *Biochemistry*, 24:4826–4844, 1985.

Caffrey and Bilderback, "Kinetics of the main phase transition of hydrated lecithin monitored by real–time x–ray diffraction," *Biophys.J.*, 45:627–631, Mar. 1984.

Chattopadhyay, "Chemistry and biology of N–(7–nitrobenz–2–oxa–1,3–diazol–4–yl)–labeled lipids: fluorescent probes of biological and model membranes," *Chem. Phys. Lipids*, 53:1–15, 1990.

Dao, McIntyre, Sleight, "Large–scale preparation of asymmetrically labeled fluorescent lipid vesicles," *Anal. Biochem.*, 196:46–53, 1991.

de Gennes, "Conformations of polymers attached to an interface," *Macromolecules*, 13:1069–1075, 1980.

Fattal, Nir, Parente, Szoka Jr., "Pore–Forming Peptides Induce Rapid Phospholipid flip–flop in membranes," *Biochemistry*, 33:6721–6731, 1994.

Gombotz and Pettit, "Biodegradable polymers for protein and peptide drug delivery," *Bioconjugate Chem.*, 6:332–351, 1995.

Gregoriadis, "Fate of injected liposomes: observations on entrapped solute retention, vesicle clearance and tissue distribution in vivo," *In: Liposomes as Drug Carriers*, Wiley, New York, pp. 3–18, 1988.

Griffin, "Calculation of "HLB" values of nonionic surfactants," *J. Soc. Cosmetic Chemists*, 1:311–326, 1949, as cited in *Biological Abstracts*, 27:1955, column 9941.

Griffin, "Calculation of "HLB" values of nonionic surfactants," *Am. Perfumer Essential Oil Rev.*, 65(5):26–29, 1955, as cited in *Biological Abstracts*, 27:1955, column 9941.

Herbette, Marquardt, Scarpa, Blasie, "A direct analysis of lamellar x–ray diffraction from hydrated oriented multilayers of fully functional sarcoplasmic reticulum," *Biophys. J.*, 20:245–272, 1977.

Hope, Bally, Webb, Cullis, "Production of large unilamellar vesicles by a rapid extrusion procedure. Characterization of size distribution, trapped volume and ability to maintain a membrane potential," *Biochem. Biophys. Acta*, 812:55–65, 1985.

Hristova and Needham, "Physical properties of polymer–grafted bilayers," *In: Stealth® Liposomes*, Lasic and Martin eds., CRC Press, Boca Raton, FL, Ch. 5, pp. 35–49, 1995.

Kenworthy, Hristova, Needham, McIntosh, "Range and magnitude of the steric pressure between bilayers containing phospholipids with covalently attached poly(ethylene glycol)," *Biophys. J.*, 68:1921–1936, May 1995.

Kenworthy, Simon, McIntosh, "Structure and phase behavior of lipid suspensions containing phospholipids with covalently attached poly(ethylene glycol)," *Biophys. J.*, 68:1903–1920, 1995.

Kenworthy, Simon, McIntosh, "Effects of lipids with covalently attached polyethylene glycol on distearolyphosphatidylcholine bilayer structure," *Biophysical Journal, 38th Annual Meeting of the Biophysical Society*, New Orleans, Louisiana, USA, Mar. 6–10, 1994.

Klibanov, Maruyama, Beckerleg, Torchilin, Huang, "Activity of amphipathic poly(ethylene glycol) 5000 to prolong the circulation time of liposomes depends on the liposome size and is unfavorable for immunoliposome binding to target," *Biochim. Biophys. Acta*, 1062:142–148, 1991.

Klibanov, Maruyama, Torchilin, Huang, "Amphipathic polyethyleneglycols effectively prolong the circulation time of liposomes," *FEBS Lett.*, 268(1):235–237, 1990.

Kuhl, Leckband, Lasic, Israelachvili, "Modulation of interaction forces between bilayers exposing short–chained ethylene oxide headgroups," *Biophys. J.*, 66:1479–1488, 1994.

Lasic, "Sterically stabilized vesicles," *Angew. Chem. Int. Ed. Engl.*, 33:1685–1698, 1994.

Lasic and Barenholz, eds., "F. Liposomes in drug delivery," *In: Handbook of Nonmedical Applications of Liposomes, From Gene Delivery and Diagnostics to Ecology*, CRC Press, Boca Raton, FL., vol. IV, pp. 308–309, 1996.

Lasic, Martin, Gabizon, Huang, Papahadjopoulos, "Sterically stabilized liposomes *: a hypothesis on the molecular origin of the extended circulation times," *Biochim. Biophys. Acta*, 1070:187–192, 1991.

Lasic, Woodle, Martin, Valentincic, "Phase behavior of >>stealth®–lipid<<–lecithin mixtures," *Periodicum Biologorum*, 93(2):287–290, 1991.

Lefkowitz, Stadel, Caron, "Adenylate cyclase–coupled beta–adrenergic receptors. Structure and mechanisms of activation and desensitization," *Ann. Rev. Biochem.*, 52:159–186, 1983.

Lesieur, Grabielle–Madelmont, Paternostre, Ollivon, "Study of size distribution and stability of liposomes by high performance gel exclusion chromatography," *Chem. Phys. Lipids*, 64:57–82, 1993.

Liu and Huang, "Small, but not large, unilamellar liposomes composed of dioleoylphosphatidylethanolamine and oleic acid can be stabilized by human plasma," *Biochemistry*, 28:7700–7707, 1989.

MacDonald, MacDonald, Menco, Takeshita, Subbarao, Hu, "Small–volume extrusion apparatus for preparation of large, unilamellar vesicles," *Biochem. Biophys. Acta*, 1061:297–303, 1991.

Marsh, "X–ray diffraction data," *In: CRC Handbook of Lipid Bilayers*, CRC Press, Boca Raton, FL, Ch. II.8, pp. 163–183, 1990.

Mayer, Hope, Cullis, "Vesicles of variable sizes produced by a rapid extrusion procedure," *Biochim. Biophys. Acta*, 858:161–168, 1986.

McIntosh, Magid, Simon, "Steric repulsion between phosphatidylcholine bilayers," *Biochem.*, 26:7325–7332, 1987.

Mori, Klibanov, Torchilin, Huang, "Influence of the steric barrier activity of amphipathic poly(ethyleneglycol) and ganglioside $GM_1$ on the circulation time of liposomes and on the target binding of immunoliposomes in vivo," *FEBS Lett.*, 284(2):263–266, Jun. 1991.

Navarro, Chabot, Sherrill, Aneja, Zahler, Racker, "Interaction of duramycin with artificial and natural membranes," *Biochemistry*, 24(17):4645–4650, 1985.

Needham, McIntosh, Lasic, "Repulsive interactions and mechanical stability of polymer–grafted lipid membranes," *Biochim. Biophys. Acta*, 1108:40–48, 1992.

Neugebauer, "Detergents: an overview," *Methods in Enzymology*, 182:239–252, 1990.

Nishikawa, Arai, Inoue, "Scavenger receptor–mediated uptake and metabolism of lipid vesicles containing acidic phospholipids by mouse peritoneal macrophages," *J. Biol. Chem.*, 265(9):5226–5231, Mar. 25, 1990.

Nolan, Magargee, Posner, Hammerstedt, "Flow cytometric analysis of transmembrane phospholipid movement in bull sperm," *Biochemistry*, 34:3907–3915, 1995.

Parr, Ansell, Choi, Cullis, "Factors influencing the retention and chemical stability of poly(ethylene glycol)–lipid conjugates incorporated into large unilamellar vesicles," *Biochim. Biophys. Acta*, 1195:21–30, 1994.

Parsegian, Rand, Fuller, Rau, "Osmotic stress for the direct measurement of intermolecular forces," *Methods Enzymol.*, 127:400–416, 1986.

Rand and Luzzati, "X–ray diffraction study in water of lipids extracted from human erythrocytes," *Biophys. J.*, 8:125–137, 1968.

Small, "Polar lipids," *In: Handbook of Lipid Research, The Physical Chemistry of Lipids, From Alkanes to Phospholipids*, Plenum Press, New York, Ch. 4, p. 93, 1986a.

Small, "Phospholipids," *In: Handbook of Lipid Research, The Physical Chemistry of Lipids, From Alkanes to Phospholipids*, Plenum Press, New York, Ch. 12, pp. 475–522, 1986b.

Szoka, Olson, Heath, Vail, Mayhew, Papahadjopoulos, "Preparation of unilamellar liposomes of intermediate size (0.1–0.2$\mu$m) by a combination of reverse phase evaporation and extrusion through polycarbonate membranes," *Biochim. Biophys. Acta*, 601:559–571, 1980.

Szoka Jr. and Papahadjopoulos, "Procedure for preparation of liposomes with large internal aqueous space and high capture by reverse–phase evaporation," *Proc. Natl. Acad. Sci. U.S.A.*, 75(9):4194–4198, Sep. 1978.

Winterhalter and Lasic, "Liposome stability and formation: Experimental parameters and theories on the size distribution," *Chem. Physics Lipids*, 64:35–43, 1993.

Woodle, "Surface–modified liposomes: assessment and characterization for increased stability and prolonged blood circulation," *Chem. Physics Lipids*, 64:249–262, 1993.

Woodle and Lasic, "Sterically stabilized liposomes," *Biochim. Biophys. Acta*, 1113:171–199, 1992.

Woodle, Engbers, Zalipsky, "New amphipatic polymer–lipid conjugates forming long–circulating reticuloendothelial system–evading liposomes," *Bioconjugate Chem.*, 5(6):493–496, 1994.

Woodle, Matthay, Newman, Hidayat, Collins, Redemann, Martin, Papahadjopoulos, "Versatility in lipid compositions showing prolonged circulation with sterically stablized liposomes," *Biochim. Biophys. Acta*, 1105:193–200, 1992.

Worthington, "The interpretation of low–angle x–ray data from planar and concentric multilayered structures. The use of one–dimensional electron density strip models," *Biophys. J.*, 9:222–234, 1969.

Yatvin, Tegmo–Larsson, Dennis, "Temperature– and pH–sensitive liposomes for drug targeting," *Methods in Enzymology*, 149:77–87, 1987.

Zalipsky, "Functionalized poly(ethylene glycol) for preparation of biologically relevant conjugates," *Bioconjugate Chem.*, 6:150–165, 1995.

\* cited by examiner

AMPHIPHILIC MATERIALS AND LIPOSOME FORMULATIONS THEREOF

The present application is a divisional application of U.S. application Ser. No. 08/912,978, filed Aug. 13, 1997, which claims priority to provisional application Ser. No. 60/024,382, filed Aug. 14, 1996, the entire text and figures of which disclosure are specifically incorporated herein by reference without disclaimer.

BACKGROUND OF THE INVENTION

1. Field of the Invention

The present invention relates generally to the fields of lipid biochemistry and liposomes. More particularly, the invention provides amphiphilic molecules that incorporate a hydrophilic material or polymer attached to two or more spatially distinct hydrophobic residues. On contact with water, these amphiphilic molecules display surface activity and self-assemble into multimolecular aggregates and liquid crystalline phases. The invention thus also provides liposomes of enhanced stability that incorporate such amphiphilic molecules, and methods of using these formulations in a variety of applications in the fields of drug delivery, nutrition, bio-diagnostics, cosmetics, blood products and related applications.

2. Description of Related Art

Amphiphilic molecules are so named because the structures contain hydrophilic and lipophilic (hydrophobic) parts. The molecules distribute across air-water and oil-water interfacial boundaries and display surface activity. In oil and water mixtures, these help form and stabilize emulsions and co-dissolve other materials. When dispersed in water at concentrations above critical solubility limits, these can be induced to self assemble into a variety of spatially ordered molecular aggregates including micelles and lamellar bilayers which can entrap other molecules in the lipid and/or the aqueous compartments of the aggregates. Amphiphile-containing emulsions, micelle, and lipid lamellar bilayer aggregates are important vehicles for parenteral delivery of therapeutic agents and nutrients.

Liposomes are spherical vesicles of self-closed hydrated bilayers of amphiphilic lipids surrounding a generally central inner aqueous phase core which can differ in composition from the extraliposomal aqueous medium (Bangham and Horne, 1964). The lipid chains may be liquid-crystalline or solid-like gel phases. Liposomes are colloidal particles ranging in diameter from 20 nm to 5000 nm. Depending on the size and the number of constituent lamellar layers, these are classified as small or large unilamellar vesicles, and as multilamellar vesicles. The multilamellar vesicles have additional water layers trapped adjacent to the hydrophilic ends (polar head groups) between the regular dual arrays of the lipophilic (hydrophobic) alkyl chains (fatty tails).

The lipid bilayer of the unilamellar vesicles is akin in composition and structure to the outer membrane of eukaryotic cells. The vesicle bilayer provides a significant controllable barrier to the movement of various molecules and ions between the inner aqueous core and the bulk aqueous phase surrounding the liposome (Bangham et al., 1965). This barrier function is paramount in many applications including drug delivery vehicles.

The need for and importance of a functional barrier is well illustrated by potential applications of liposomes in enzyme replacement therapies for inherited metabolic diseases, in other therapies using bioactive peptides and proteins, and in hemoglobin-based blood substitutes. The safety and efficacy of therapeutic/bioactive proteins depends upon their ability to overcome metabolic and transport barriers and reach the target site in a biologically active form. This in turn is dependent on the route for administration.

In general, exogenous proteins cause immunogenic and antigenic reactions and undergo rapid hydrolytic degradation in vivo. These problems can be partially alleviated by modification of the protein by covalent conjugation to a biocompatible hydrophilic polymer such as a monofunctional polyethyleneglycol (PEG). As an example, adenosine deaminase conjugated to ω-methyl-polyethyleneglycol (MePEG) of average molecular weight 5000 shows lower immunogenicity and antigenicity, and prolonged blood circulation half-life. However, although the conjugate has seen some clinical use, it has relatively low enzyme activity (Beauchamp et al., 1983). Despite the loss of bioactivity on covalent modification of proteins that is known to occur generally, other MePEG-linked proteins, including the inimunoregulatory cytokine interleukin-2, and the oxygen transporter hemoglobin, are being investigated for ultimate use in vivo.

The extra effort needed to develop reasonably active conjugates for every enzyme contemplated for in vivo is a significant limitation in this field. This could be avoided if an encapsulation process applicable to all unmodified enzymes could be developed, but this has yet to be achieved. Potential systemic and transdermal delivery systems for unmodified bioactive proteins, such as entrapment in biodegradable microspheres fabricated from poly(lactide-co-glycolide) and other polymers, are being investigated (Gombotz and Pettit, 1995). Liposomal systems have also been proposed and, although these offer the advantage that they are capable of self-assembly (Gregoriadis, 1988), they currently suffer from certain drawbacks.

Liposomes are normally prepared from natural phospholipids and synthetic analogues such as the electrical charge neutral zwitterionic phosphatidylcholines. Minor proportions of anionic phospholipids, such as phosphatidylglycerols, are added to generate a net negative surface charge for colloid stabilization. The lipid chains in the bilayer may be present as crystalline or mesophase (liquid-crystalline) states. The type of mesophase controls the physical integrity of the liposomes in vitro and in vivo, and liposomes with gel phase bilayers are more stable in blood than those with liquid-crystalline bilayers.

For liposomes administered parenterally, the blood circulation half-life, distribution and disposition in organs and tissues is correlated strongly with the diameter and the surface properties of the liposomes. Most liposomes are rapidly taken up by the phagocytic cells of the reticuloendothelial system (RES), the circulating mononuclear phagocytic cells and those located in the liver and spleen, and their blood circulation half-lives are short (a few minutes). This uptake is generally mediated by binding of plasma proteins (opsins) to the liposomal surface. The non-specific "scavenger receptor" that recognizes negative charges in large arrays may be involved also (Nishikawa et al., 1990). Liposomes smaller in diameter than the average diameter of the fenestrae in the blood capillaries leak out. The average diameter of the fenestrae in the imperfectly formed sinusoids in rapidly growing tumors is larger than in normal tissues and therefore liposomes smaller than about 100 nm in diameter migrate into tumors.

The above two proclivities provide the basis for targeting liposome-encapsulated drugs to liver and tumors respectively. A primary requirement for targeting therapies for metabolic disorders to other organs and tissues is that liposomes be able to evade uptake as above and have long blood circulation half-life. The inclusion of ganglioside $G_{M1}$, a natural glycolipid with terminal sialic acid residue, as a minor envelope component improves circulation life, presumably because of changes in the liposomal surface characteristic (Allen and Chonn, 1987). However, this has yet to yield sufficiently beneficial results.

Recently, certain ω-methyl-polyethyleneglycol-conjugated anionic lipids have been developed, notably ω-Me-PEG-phosphatidylethanolamines (MePEG-PE), and used as envelope components at about 5 mole % of total lipid. The resulting liposomes display pendant MePEG residues on the outer lipid envelope surface, and these are considered to act as steric barriers to opsin attachment and RES uptake (Lasic et al., 1991; Needham et al., 1992; Woodle and Lasic, 1992). Therefore, these liposomes are called sterically stabilized liposomes. The degree of polymerization and surface density of the MePEG, and anionic charge are important parameters for liposome stability. However, even with optimum parameters, these sterically stabilized liposomes only have a blood circulation half-life of between about 12 and about 48 hours, as compared to the blood circulation half-life of red blood cells of 28 days.

Antibodies and receptor-specific ligands have also been tethered to the surface of sterically stabilized liposomes for inducing targeted delivery to specific tissues. Counterproductively, the pendant MePEG chains in these mixed surface ligand type liposomes not only prevent uptake by the RES but also hinder the approach and binding of liposome-surface-linked antibodies to the target tissue receptors. Therefore, the art is, at best, ambivalent about their potential for targeted delivery to specific tissues. For instance, according to an authoritative comment "the remaining problems of accessibility of a particular tissue and cells as well as overlooked severity of triggering an immune response to the host organism by antibody or lectin-coated liposomes makes this goal rather remote at present" (Lasic and Barenholz, 1996).

In an attempt to generate liposomes of improved stability, two broad trends are discernible in the current research literature. There is continuing interest in (i) optimizing existing liposome types, and (ii) in developing alternative systems. Optimization is being attempted by the development of alternatives lipid conjugates of MePEG. The preparation and applications of diacylglycerol and cholesterol in place of PE, and for the MePEG-PE series, the investigation of different spacers and chemistries for conjugating MePEG to PE have been described (Parr et al., 1994; Zalipsky, 1995). However, these have still not countered the prevailing pessimism explained above. Alternatively, various hydrophilic polymers other than MePEG have been conjugated to PE, but only poly(2-methyl-2-oxazoline) and poly(2-ethyl-2-oxazoline) conjugates have afforded even the minimum protection from hepatosplenic uptake seen with MePEG-PE (Woodle et al., 1994).

Data on the retention and chemical stability of MePEG-lipid conjugates incorporated into unilamellar vesicles are available. Many MePEG-lipid stabilized liposomes gave very little improvement in circulation half-life, and this was traced to the rapid removal of the hydrophilic coating. The latter is attributed to the loss of the intact MePEG-lipid from the liposomal membrane. Significant chemical breakdown of MePEG-lipid (MePEG-PE) occurs, especially after its detachment from the liposome body. Finally, the loss of hydrophilic coating precedes liposome clearance (Parr et al., 1994).

Focusing on the properties inherent in the MePEG-lipid conjugate structure, the present inventor has reevaluated these data in terms of relative propensity of the conjugate for retention in the liposome bilayer and proclivity for migration into the extraliposomal fluid, and, the mole % of MePEG-lipid in the bilayer phospholipids needed for complete coverage with an adequate depth of MePEG chains. For representative phospholipid structures, conjugates with relatively short MePEG chains tend to stay in the bilayer but provide inadequate surface barrier. Conjugates with longer chains tend to migrate into the surrounding aqueous medium, particularly at high concentrations which provide adequate surface barrier. The inventor realized that the balance of these opposing influences/conflicting constraints cannot be improved further without a radical departure from the structures typified by MePEG-lipid. In particular, these efforts cannot provide the minimum one order of magnitude increase in half- life needed for encapsulated functional proteins such as hemoglobin for blood substitutes.

SUMMARY OF THE INVENTION

The present invention overcomes the foregoing and other drawbacks inherent in the prior art by providing a range of new synthetic amphiphilic materials of a unique molecular structural class. The structural motif of the amphiphilic materials of the invention results from the combination of a hydrophilic residue, compound or polymer, that is attached to two or more hydrophobic residues or moieties at spatially distinct sites on the hydrophilic residue. In certain embodiments, the two or more hydrophobic moieties are attached to the hydrophilic residue at distinct sites of an intermediate or wide spatial distance, such that they are attached at 'spatially distant' sites.

The hydrophilic compound or polymer is preferably non-immunogenic, for example, a polyethylene glycol, and may additionally contain functional groups for attaching agents other than the hydrophobic residues. The hydrophobic residues or moieties are preferably lipids, such as phosphatidyl, that can intercalate in the lipid bilayer array of conventional liposomes. The hydrophobic moieties are preferably covalently attached to the hydrophilic compound or polymer, such as by using an ester, ether, or other selected bond-type.

The amphiphilic materials of the invention form lyotropic self-assembled multimolecular aggregate phases alone and in mixtures with conventional amphiphiles (for instance phosphatidylcholines) on interaction with aqueous media. The hydrated hydrophilic polymer segments of the molecular structure are oriented around the lipid segment of the lyotropic self-assembly in a topography reminiscent of canopies and staples.

The novel amphiphiles provided by the invention and the derived self-assembled aggregates have utility generally as processing-aids, e.g., emulsifiers, and as functional ingredients in products fabricated as lipid- microemulsion-, micelle-, and liposome-based protective delivery vehicles for use in agriculture, diagnostics, drug, food, nutrition, personal-care and hygiene products, and, industrial applications.

The unique interfacial topography makes these novel amphiphilic materials and the derived self-assembled aggregates particularly appropriate for application in liposomal and micellar preparations suitable for passive and targeted drug delivery and antigen-presentation for diagnostics. The unique topography may be engendered additionally by equilibrating the hydrated novel amphiphiles with preformed liposomes and biological cells to create non-immunogenic red blood cells for blood substitutes and analogous biomaterials.

Accordingly, the present invention provides an amphiphilic molecule comprising a hydrophilic compound, polymer or polymer residue having attached, at spatially distinct sites, at least two hydrophobic moieties. The hydrophilic compounds of these molecules may be polymers or polymeric residues, such that the compounds are constructed from repeating units of individual monomers; may be co-polymers comprised of ordered or random repeating units of two or more individual monomers; or may be any other suitable hydrophilic compound that permits the operative attachment of the hydrophobic moieties.

The two or more hydrophobic moieties are attached to the hydrophilic compound at "spatially distinct sites". The spatially distinct attachment means that the at least two hydrophobic moieties must be attached to distinct attachment sites of the hydrophilic compound or polymer, and are not formed by extending a first hydrophobic moiety by direct attachment to a second hydrophobic moiety (forming a single extended chain). The hydrophobic moieties or residues are therefore appended to the hydrophilic compound or polymer, and are not attached to each other.

The spatially distinct attachment sites on the hydrophilic compound are sites that are adapted to receive the hydrophobic moieties. This means that the attachment sites are capable of physical and functional attachment to a hydrophobic moiety and are separated from one another such that the attachment of a first hydrophobic moiety to a first attachment site on the hydrophilic compound does not impair the physical and functional attachment of a second hydrophobic moiety to the nearest or second attachment site on the hydrophilic compound.

In certain embodiments, it may be that the spatially distinct attachment sites are separated by only a single carbon atom. In other embodiments, the hydrophobic moieties or residues will be attached to the hydrophilic compound or polymer at spatially distinct sites of increasing distance, which distances may be termed as short, moderate, intermediate, long or maximal distances. In general, short spatial distances will be on the order of between about 1, 2, 3, 4 or 5 carbon atoms in length, or the equivalent distance as spanned by other chemical constituents of the hydrophilic compound or polymer. The spatially distinct attachment sites may be separated by lengths directly corresponding to or equivalent to lengths of carbon atoms of between about 5, 10, 15, 20, 25, 50, 100, 150, 250, 500, 1000 or so.

The spatially distinct attachment sites may also be described in reference to their geometrical location along a hydrophilic compound or polymer. For example, the attachment sites may be located at one or more terminal portions of a hydrophilic compound or polymer, generally proximal to such terminal compounds, spaced equidistant along a hydrophilic compound or polymer, clustered in one region of the hydrophilic compound or polymer, randomly distributed along the hydrophilic compound or polymer, and the like. The spatially distinct attachment sites may also be understood with reference to each of FIG. 1, FIG. 3, FIG. 4, FIG. 7 and FIG. 8.

In certain preferred embodiments, the two or more hydrophobic moieties will be attached at spatially distinct sites in order to impart a defined property to the resultant amphiphilic molecule. In other embodiments, the hydrophobic moieties may be randomly attached throughout a hydrophilic compound in order to prepare an amphiphilic molecule with a plurality of hydrophobic moieties. In the first group of embodiments, one may elect to attach two or more hydrophobic moieties to attachment sites that are separated by moderate or intermediate distances, such that the resultant amphiphilic molecules will be able to associate with a lipid bilayer in a desired manner. For example, attachments at, proximal to, or in the region of the termini of a hydrophilic compound or polymer will result in an amphiphilic molecule capable of integrating into a bilayer generally as shown in FIG. 5.

Those of skill in the art will appreciate that, in general, attaching two or more hydrophobic moieties to a defined spatial region of a hydrophilic compound will promote closer association of that portion of the hydrophilic compound to a lipid bilayer upon admixture. Equally, widely separating the hydrophobic moieties at spatially distant attachment sites will result in an amphiphilic molecule in which the hydrophilic compound is more likely to be more flexibly associated with a bilayer or to have intervening regions that are able to migrate to some distance of the bilayer (either in loops or as inverted tear-drops), while the amphiphilic molecule as a whole remains in association with a bilayer by virtue of attachment through said two or more hydrophobic moieties.

In certain embodiments, the invention provides an amphiphilic molecule comprising a hydrophilic compound, polymer or polymeric residue and at least a first and a second hydrophobic moiety or residue, the first and second hydrophobic moieties being attached to said hydrophilic compound at distinct first and second attachment sites. As set forth above, the first and second attachment sites may be proximal to each other, at intermediate distances along the polymer, or widely distant from each other, including being distant from each other for the entire length of the molecule such that they are attached at each terminus.

The amphiphilic molecules of the invention or "amphiphiles" will preferably include a biocompatible hydrophilic compound or polymeric residue when the resultant amphiphile is intended for use in veterinary, medicinal or other biomedical applications. By the term "biocompatible", is meant that the hydrophilic compound and the resultant amphiphilic molecule do not elicit significant adverse or untoward reactions upon administration to the particular animal in which they are intended for use. Determinations of biocompatibility are readily made by those of ordinary skill in the art, and include assessing the known properties of compounds, as described in the scientific literature, prior to generating an amphiphilic molecule and the testing of the molecule in appropriate in vitro and in vivo studies.

It will be appreciated that different biocompatible polymers and resultant amphiphiles may be prepared for use in distinct embodiments. For example, for use in cosmetic or other external medical or veterinary applications, the polymer and amphiphile are required to be generally dermatologically safe and not to elicit significant adverse reactions upon contact or repeated contact with the skin. Similar concerns are applied to amphiphiles for internal use, during which use they should not cause significant systemic or local toxicity in the animal or human subject. Such considerations apply equally to the hydrophobic moieties for attachment to create the resultant amphiphile.

The hydrophilic compounds, polymers or polymer residues for use in the invention may be substantially linear, linear, partially branched, highly branched or a pendant or star hydrophilic compound or polymer. Suitable examples of such polymers are described herein, with particular reference to the appended figures and to Table 1. Any of the individual compounds listed within Table 1 and known to those of skill in the art may be further joined to create a hybrid or conjugate hydrophilic compound.

To be "hydrophilic" in the context of the present invention, the compound or polymer is required to have measurable solubility in water, preferably of at least about 10%, 20%, 30% or so, or even greater, and should also preferably be soluble in certain organic solvents.

The hydrophilic compound or polymer components of the amphiphiles will preferably have an average molecular weight of between about 100 and about 100,000 daltons, with all intermediate molecular weights between these ranges being contemplated. For example, an appropriate hydrophilic compound for use herewith may have an average molecular weight of about 100, 200, 500, 1,000, 2,000, 5,000, 10,000, 20,000, 50,000, 75,000 and about 100,000 or more. In certain preferred embodiments, the molecular weight of the hydrophilic component will be between about 100 and about 20,000, between about 100 and about 10,000, between about 2,000 and about 20,000, between about 2,000 and about 10,000, or between about 100 and about 10,000 or so.

In certain preferred embodiments, the hydrophilic compound of the amphiphile will be a polyethylene glycol (PEG). Other preferred compounds are polyvinyl pyrrolidone and polyethyleneimine.

The "hydrophobic moieties or residues" are preferably hydrophobic components that are sterically compatible with typical lamellar lipid bilayers, such that they are capable of spontaneously forming bilayers, or intercalating into bilayers, and are generally selected so as to achieve a good steric fit without significant perturbation of the normal packing geometry of lamellar bilayers. A wide variety of such molecules are known to those of skill in the art and are suitable for use herewith.

In general terms, hydrophobic residues of short, medium or long lipid chains may be employed. Short chain lipids generally have less than about eight carbon atoms (8C). Where such short chain hydrophobic moieties are employed, it may be advantageous to employ a moderate amount of such residues in order to provide an amphiphile molecule with a plurality of appended short chain lipids.

In more preferred embodiments, it is believed that advantages will result from the use of hydrophobic residues having between about 8 carbon atoms (8C) and about 26 carbon atoms (26C), with those having between about 12 carbon atoms (12C) and about 20 carbon atoms (20C) being generally preferred.

A wide variety of hydrophobic compounds are available in the art, any one or more of which may be used to advantage in the present invention. These are exemplified by single, double, multiple, linear and branched chain hydrophobic moieties. Certain exemplary hydrophobic moieties are included herewith in Table 2. For example, the hydrophobic moiety may be an alkylether, fattyester, dialkylglycerol, alkylamino, dialkylamino, diacylglycerol, sphingolipid, synthetic cationic lipid precursor, sterol, cholestanic acid, a phospholipid or perfluoro analog thereof. In other embodiments, one or more or a combination of the following compounds may be employed: 1,2-distearoylglycerol or 1,2-dioleoylglycerol, ceramidophosphoric acid or O-acetyl-ceramidophosphoric acid, 1,2-dioleyl-3-dimethylaminopropanediol, 1,2-dimyristoyl-3-dimethylaminopropanediol, cholesterol or β-sitosterol, distearoyl phosphatidic acid, dioleylphosphatidic acid, a bisphosphatidyl glycerol, phosphatidylethanolamine or a phosphatidylinositol.

In the amphiphilic molecules of the invention, the hydrophilic compound may be operatively attached to only two hydrophobic moieties. In other embodiments, the hydrophilic compound may be attached to at least 2, at least 3, at least 5, at least 10, at least 15 or at least about 20 or so hydrophobic moieties. The hydrophilic compound or polymer may thus be attached to 2, about 3, 4, 5, 6, 7, 8, 9, 10, 11, 12, 13, 14, 15, 16, 17, 18, 19, 20, 21, 22, 23, 24, 25 or to about 30 or to about 40 or so hydrophobic moieties. The amphiphiles thus include ranges of hydrophobic appendages of between 2 or about 3 and about 40 or so, 30 or so, 20 or so; between about 5 and about 20, between about 5 and about 10, and all intermediates within the foregoing stated ranges.

In certain embodiments, the invention provides amphiphilic molecules comprising a hydrophilic compound or polymer that is operatively attached to a plurality of hydrophobic moieties. In attaching a plurality of hydrophobic moieties or residues to a given hydrophilic compound, those of ordinary skill in the art will appreciate, in light of the present disclosure, that a balance is to be achieved between the hydrophilic and hydrophobic moieties in order to achieve an amphiphile with the desired properties. A particularly preferred property is the ability of the resultant amphiphile to achieve a desired micellar or lamellar mesophase upon interaction with an aqueous medium, such as water.

The invention includes amphiphilic molecules of a bipodal nature, in which the amphiphile comprises only two hydrophobic moieties. Such bipodal amphiphiles may comprise a substantially linear or linear hydrophilic compound or polymer comprising a first and second hydrophobic moiety, the first and second hydrophobic moieties being separately attached to spatially distant attachment sites on said hydrophilic compound, including those embodiments in which the hydrophobic moieties are separately attached to the first and second terminus of the hydrophilic compound, respectively. In other bipodal embodiments, only one of said at least two hydrophobic moieties need be attached at, proximal to, or substantially at one terminus of the hydrophilic compound. Linear polymers need not be used, but these may be preferred for simplicity.

Tripodal amphiphilic molecules are also provided, in which a hydrophilic compound has a first, second and third hydrophobic moiety separately attached thereto. The tripodal amphiphiles may have a three-way symmetry, in which the amphiphilic molecule comprises a branched hydrophilic compound having at least three termini, and wherein the first, second and third hydrophobic moieties are separately attached at, or proximal to, three of said at least three termini.

Oligopodal amphiphiles are also provided, which comprise at least about five or so hydrophobic moieties in conjunction with said hydrophilic compound. The oligopodal compounds may comprise a linear or substantially linear hydrophilic base, or may comprise a moderately branched hydrophilic compound or polymer. In embodiments where a branched compound is employed, five or ten or so hydrophobic moieties may be attached at the termini resulting from each branching chain.

In a similar manner, the invention provides polypodal amphiphilic molecules comprising a plurality of hydrophobic moieties attached to a hydrophilic compound. The compound may again be linear, although the polypodal embodiments are well served by the use of a branched or star hydrophilic compound (e.g., FIG. 4). Again, where a branched or star hydrophilic polymer is employed, a plurality of termini will be available for attachment to a hydrophobic moiety. Depending on the degree of branching of the hydrophilic compound, at least about 10%, 20%, 50%, 75%, 90% or 95% of said termini may be separately occupied by a hydrophobic molecule. Polypodal amphiphiles are also contemplated in which every terminus of a branched or star hydrophilic compound is occupied by an attached hydrophobic moiety.

It will be appreciated that the amphiphilic molecules may comprise two or more identical hydrophobic moieties up to and including a plurality of hydrophobic moieties each of the same molecular type. Alternatively, the amphiphiles may comprise two non-identical hydrophobic species, again up to and including a plurality of hydrophobic species in which each particular appended hydrophobic molecule is of a separate molecular type. All such variations are encompassed within the scope of the invention.

In preferred embodiments, it is contemplated that at least one of said hydrophobic residues will be covalently attached to said hydrophilic compound or polymer residue. In other preferred embodiments, each of said at least two hydrophobic moieties will be attached to the hydrophilic compound via a covalent bond.

Therefore, the invention provides, in part, an amphiphilic molecule comprising a hydrophilic compound having attached, at spatially distinct or distant sites, at least two hydrophobic moieties, wherein at least one of said two hydrophobic moieties are covalently attached to the hydrophilic compound. Also provided are amphiphiles comprising a hydrophilic compound having covalently attached, at spatially distinct or distant sites, at least two hydrophobic moieties. In embodiments where more than two hydrophobic moieties are included within the amphiphile, any two or more of such residues may be covalently attached, and the invention extends the covalent attachment of each hydrophobic moiety to the hydrophilic supporting compound.

However, covalent attachment is not the only means of attaching the two or more hydrophobic moieties to the core hydrophilic compound. For example, non-covalent attachment means may be employed, such as those depending on ionic salt interactions or molecular adducts, such as provided by the tight binding of biotin and avidin. Other receptor-ligand interactions may also be employed. The covalent attachment of at least one of the hydrophobes is particularly preferred, and the covalent attachment of at least two hydrophobes is also a preferred aspect of the invention.

The covalent attachment may be via a direct covalent bond or via a "molecular spacer", such as a peptide spacer or other bridging molecule. In certain embodiments, one or more of the hydrophobic moieties may be attached to the central hydrophilic compound via a biologically releasable bond. Such bonds include those metabolizable by non-specific chemical or enzymatic pathways, and also those preferentially cleavable under certain conditions, such as occurs upon localization to a specific biological site within the body.

It will also be appreciated that more stable covalent bonds may be used to advantage in formulations that are intended for oral administration or for industrial applications. For example, the alkyl ether type linkages are relatively stable, particularly to hydrolytic enzymes, and are suitable for use in such embodiments.

The range of preferred covalent bonds contemplated for use herewith include alkylamine, alkylamonium, carbamate, amide, ether, ester and phosphodiester bonds.

In certain embodiments, the hydrophilic compound or polymer residue will be first derivatized to introduce at least one functional group permitting the attachment of at least one of said hydrophobic moieties via a covalent bond. The hydrophilic compound may thus be derivatized to introduce at least one aldehyde, thiol, alkyl, dialkylamino, amino, carboxyl, or polyol functional group. In certain embodiments, the derivatization of a hydrophilic compound to produce a methanesulfonate ester of an alcohol group present on the hydrophilic compound is particularly preferred.

In further embodiments, the hydrophilic compound may further comprise a selected agent attached at a site distinct from said at least two hydrophobic moieties. Exemplary agents that may be attached in this manner are antibodies and antigens against which one desires to raise a humoral or cellular immune response. Other appropriate molecules are ligands for biological receptors, or in reciprocal embodiments, one or more biological receptor molecules.

An advantageous aspect of the present invention is that the amphiphilic molecules disclosed herein spontaneously form liquid crystalline multimolecular aggregates upon hydration. Therefore, when formulated with a population of like molecules in an aqueous solution, the novel amphiphiles of the invention self assemble into molecular aggregates and supra molecular assemblies, including micelles, monolayers, bilayers, multimolecular aggregates, lipid microemulsions formulated into a micelle, monolayer, bilayer, multimolecular aggregate, lipid microemulsion, oil globules, fat globules, wax globules, synthetic microreservoirs and liposomes. The self assembly or formulation into such macromolecular assemblies is a surprising feature of this invention. Therefore, the amphiphiles or populations thereof may be advantageously contacted with or dispersed within solvents or liquids, including polar liquids, such as water-based solutions. They may also be formulated in non-polar solvents or liquids.

In certain preferred embodiments, the invention is defined as providing amphiphilic molecules comprising a hydrophilic compound having covalently attached, at spatially distant sites, at least two hydrophobic moieties, said amphiphilic molecule forming a liquid-crystalline multimolecular aggregate upon contact of a number of said amphiphilic molecules with an aqueous solution, wherein the mesophases of said liquid-crystalline multimolecular aggregates, as characterized by X-ray diffraction, include the fluid $L_\alpha$ and gel $L_\beta$ phases.

In still further embodiments, the invention thus provides liquid-crystalline multimolecular aggregates comprising a plurality of amphiphilic molecules dispersed in an aqueous solution, said amphiphilic molecules each comprising a hydrophilic compound having attached, at spatially distinct sites, at least two hydrophobic moieties. Preferably, the liquid-crystalline multimolecular aggregate is one wherein the mesophases of the liquid-crystalline multimolecular aggregates, as characterized by X-ray diffraction, include the fluid $L_\alpha$ and gel $L_\beta$ phases.

In other embodiments, the amphiphiles of the invention may be advantageously mixed or otherwise combined in non-covalent association with at least one distinct amphiphilic, hydrophilic or hydrophobic molecule or population thereof. The physical association of the claimed amphiphiles with populations of distinct lipid components also leads to the spontaneous assembly into multimolecular aggregates, including liposomes. Accordingly, the invention provides formulations wherein one or more of the amphiphiles of the invention is formulated with at least one or more lipid components to form a liposome or lipid complex with at least one liposome bilayer. These embodiments include formulations of small unilamellar vesicles of between about 30 and about 100 nm in diameter, large unilamellar vesicles of between about 100 and about 1,000 nm in diameter, and intermediates thereof, and also includes formulation into multilamellar vesicles.

In certain preferred embodiments, the invention provides amphiphilic molecules formulated with at least one or more lipid components to form a liposome comprising at least an outer liposome bilayer, wherein the hydrophilic compound of the amphiphilic molecule is in contact with at least a portion of said outer liposome bilayer and wherein the hydrophobic moieties of said amphiphilic molecule extend into the outer liposome bilayer. Further examples are amphiphilic molecules that comprise a plurality of hydrophobic moieties that extend into the outer liposome bilayer, wherein the hydrophilic compound extends in contact over a substantial portion of the outer liposome bilayer.

Again, the resultant liposome may be advantageously combined with other surface-available components, such that the liposome comprises at least one surface-available antibody, antigen or binding ligand dispersed in the liposome bilayer or tethered to a component of the liposome bilayer.

In yet further embodiments, the invention provides liposomes, lipid complexes or populations thereof that comprise an amphiphilic molecule that comprises a hydrophilic compound positioned over at least a portion of the outer surface of said liposome or lipid complex, the hydrophilic compound having attached, at spatially distinct sites, at least two hydrophobic moieties that extend into the hydrophobic bilayer of said liposome or lipid complex. The liposomes or complexes may also comprise amphiphilic molecules that comprise a plurality of hydrophobic moieties that extend into the hydrophobic bilayer of the liposome, wherein the hydrophilic compound is positioned over a substantial portion of the outer surface of said liposome or lipid complex. In certain embodiments, the hydrophile will extend over the complete outer surface.

In light of the ability of the amphiphilic molecules themselves to advantageously form liposomes, it will be appreciated that the liposomes of the invention include those in which the liposomal bilayer components are made up of between about 1% amphiphile and about 99–100% amphiphile. Liposomes are contemplated that comprise any amount of novel amphiphiles between the stated range, such that they may comprise 1%, 2%, 3%, 4%, 5%, 6%, 7%, 8%, 9%, 10%, 12%, 15%, 18%, 20%, 25%, 30%, 35%, 40%, 44%, 50%, 55%, 60%, 65%, 70%, 75%, 80%, 85%, 90%, 91%, 92%, 93%, 94%, 95%, 96%, 97%, 98%, 99% and about 100% amphiphile in their bilayer. In such embodiments, the preferred mode of assessing the percentage contribution of amphiphile is to use a mole percent (mole %). In certain preferred embodiments, the amphiphiles will be present in amounts between about 5 mole % and 80 mole %, between about 10 mole % and about 70 mole %, and between about 20–30–40 mole % and about 60 mole % of the total components in the liposome bilayer.

The liposomes of the invention may be formulated with any one or more of the lipid components known to those of ordinary skill in the art. By way of example only, one may mention phospholipids, such as phosphatidylcholine; sterols, such as cholesterol, sphingolipids, such as sphingomyelin; and other components such as sucrose. By means of an exemplary embodiment only, the amphiphile-containing liposomes of the invention may contain the following constituents: between about 40 mole % and about 60 mole % amphiphile; between about 20 mole % and about 30 mole % of phosphatidylcholine; between about 5 mole % and about 10 mole % of sphingomyelin; with the optional addition of other components such as gangliosides and sucrose. Again, the liposomes may comprise in their outer bilayer one or more surface-available components such as antibodies, antigens, binding ligands, receptors, or functional portions thereof. These components may be dispersed within the bilayer or covalently attached to a component thereof.

Any of the liposomes of the invention may be advantageously combined with one or more selected agents. The use of liposomes to deliver agents in medicinal embodiments is known to those of ordinary skill in the art. Accordingly, the liposomes of the invention, comprising the novel amphiphiles in any appropriate amount, may further comprise a fat soluble, water-insoluble agent or a water-soluble agent. It will be appreciated that the selected agent may be encapsulated, entrapped or otherwise physically and functionally associated with the liposome or a lipid complex or multimolecular lipid aggregate. For example, a selected hydrophilic agent may be dispersed within the aqueous phase or lumen of the liposome. Equally, a selected hydrophobic agent may be encapsulated, entrapped or otherwise dispersed within the lipid phase of the liposome. It will be appreciated that multimolecular aggregates may not comprise a lumen as such, i.e., that liposomes are not always spherical in nature and do not define a central chamber in which a selected agent will always be located.

The type of selected agent that may be functionally associated with the liposomes of the invention is virtually limitless and those of skill in the art are referred to exemplary Tables 3A, 3B and 4. By way of example only, one may mention selected pharmacological agents, such as chemotherapeutic agents or cytotoxins (Table 3B); agents to combat infectious organisms, such as antibiotics, anti-virals and fungicides, particularly amphotericin B; immunological components, such as antibodies or fragments thereof, antigens, cytokines and anti-inflammatory agents in general; enzymes, hormones and neurotransmitters, anesthetics; blood components such as hemoglobin and coagulants; and a variety of nucleic acid molecules, constructs or vectors, including those that express any of the foregoing components and those that include antisense nucleic acids and ribozymes.

In other embodiments, the selected agents may be a nutritional supplement, such as a parenteral fat emulsion, e.g., for use in critically ill animals or patients. In still further embodiments, the liposomes may comprise contrast agents as selected agents. Agents may also be employed for non-medicinal uses, and, by way of example only, one may mention pheromones.

In addition to liposomes, the present amphiphilic molecules may be used in conjunction with biological cells to form amphiphile-coated cells, such as red blood cells. In such embodiments, the amphiphilic molecule provides an outer barrier to the cell in a similar manner, wherein the hydrophilic component of the amphiphilic molecule is in contact with at least a portion of the outer surface of the cell and wherein the hydrophobic appendages extend into the outer membrane of the cell thereby anchoring the amphiphilic molecule in functional association with the cell. Red blood cells from various animals and human subjects are particularly contemplated for use in such embodiments.

In that the amphiphiles of the invention provide important barrier functions to the liposomes, complexes or cells that they are associated with, the invention also provides liposomes with increased half-life, such that the liposomes exhibit a half-life of between about one day and about five or about ten days upon incubation in a buffered solution or in a serum sample in vitro. Even half-lives of over about 48 hours or so are advantageous in comparison to half-lives obtainable with the compositions of the prior art. Techniques for analyzing the half-life of a liposome in vitro and in vivo are well known to those of ordinary skill in the art and are further disclosed in detail herein.

The present invention also provides a number of methodological embodiments. First provided is a method of making an amphiphilic molecule, comprising attaching, or preferably covalently attaching, at least two hydrophobic moieties to spatially distinct or distant attachment sites of a hydrophilic compound or polymer.

Methods of making liposomes are also provided, which generally comprise admixing, in an excess of an aqueous solution, a population of lipid components with a population of amphiphilic molecules, preferably prehydrated amphiphilic molecules, that comprise a hydrophilic compound having at least two hydrophobic moieties attached at spatially distinct sites, the admixing being effective to form a liposome. In such embodiments, the admixing is generally conducted in an aqueous solution, such as water, comprising an effective amount of each of the lipid components and amphiphilic molecules, for a period of time effective and in a manner conducive to form liposomes. Those of skill in the art will understand that the admixing manner most effective to form liposomes involves the use of sonication. The sonication is performed for a period of time effective and in a manner conducive to form liposomes that are coated by the hydrophilic component of the amphiphile, and in which the amphiphile is secured to the liposome by virtue of the hydrophobic moieties extending into their liposomal bilayer.

The present invention also provides analogous methods of making amphiphilic material-coated liposomes, complexes or biological cells, comprising contacting a liposome or biological cell with an amphiphilic material that comprises a hydrophilic compound having at least two hydrophobic moieties attached at spatially distinct sites, such that the hydrophobic moieties extend into the hydrophobic bilayer of said liposome or cell and the hydrophilic compound is positioned over at least a portion of the surface of the liposome or cell. The preferred biological cells for coating with amphiphiles are red blood cells.

The invention further provides methods for encapsulating or entrapping a selected agent in a liposome, comprising admixing a selected agent with a population of liposomes or lipid complexes that comprise an amphiphilic molecule that comprises a hydrophilic compound positioned over at least a portion of the outer surface of the liposome or complex, the hydrophilic compound having attached, at spatially distinct sites, at least two hydrophobic moieties that extend into the hydrophobic bilayer of the liposome or complex, wherein the admixing procedure is effective to cause encapsulation or entrapment of the selected agent in the liposome or lipid complex.

The foregoing methods of the invention lead to even further compositions, such as kits, cosmetic formulations and medicinal delivery compositions. These are generally provided as a kit comprising, in suitable container means, an amphiphilic molecule comprising a hydrophilic compound having attached, at spatially distinct sites, at least two hydrophobic moieties; or a liposomal formulation or lipid complex comprising said amphiphilic molecule. Such kits may further comprise one or more selected agents.

The cosmetic formulations are those comprising, in a cosmetically acceptable base, a population of liposomes or lipid complexes that comprise an amphiphilic molecule that comprises a hydrophilic compound positioned over at least a portion of the outer surface of the liposome or lipid complex the hydrophilic compound having attached, at spatially distinct sites, at least two hydrophobic moieties that extend into the hydrophobic bilayer of the liposome or lipid complex.

The medicinal delivery compositions comprise, in a pharmaceutically acceptable vehicle, a population of liposomes or lipid complexes comprising a selected agent; wherein said liposomes comprise an amphiphilic molecule that comprises a hydrophilic compound positioned over at least a portion of the outer surface of the liposome or lipid complexes, the hydrophilic compound having attached, at spatially distinct sites, at least two hydrophobic moieties that extend into the hydrophobic bilayer of the liposome or lipid complexes.

In yet still further methodological embodiments, the invention provides methods for administering a selected agent to an animal or human, comprising administering to the animal or human a medicinal delivery composition comprising, in a pharmaceutically acceptable vehicle, a population of liposomes or lipid complexes comprising the selected agent; wherein the liposomes or lipid complexes comprise an amphiphilic molecule that comprises a hydrophilic compound positioned over at least a portion of the outer surface of the liposome or lipid complexes, the hydrophilic compound having attached, at spatially distinct sites, at least two hydrophobic moieties that extend into the hydrophobic bilayer of the liposome or lipid complex. These delivery methods may be used to supply any of the selected agents described herein and equivalents thereof, including nutritional supplements, blood components, immunological components, anticancer treatment agents, anti-infectious formulations, anesthetics, enzymes, hormones or neurotransmitters for replacement therapy, and nucleic acid molecules encoding any of the foregoing components.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the illustrative embodiments presented herein.

DETAILED DESCRIPTION OF ILLUSTRATIVE EMBODIMENTS

To address the evident need in the art for new generations of stabilized liposomes, the present invention provides a range of molecular canopies, molecular staples, and kindred molecular devices for shielding and securing liposomes and other non-covalent molecular aggregates and supramolecular assemblies.

As applied to liposomes, these conceptually new and novel molecular devices are visualized as controllable biomaterial barriers positioned between liposome surface and the surrounding medium, and as clamps for enhancing lateral cohesion within lamellar bilayer domains. At the functional level, the devices are akin to barrier guards and sentinels controlling traffic between lumen contents, the liposomal membrane, and the extraliposomal milieu. Control of such trafficking is critical for applications of liposomes in biomedicine, especially as vehicles for parenteral drug delivery.

To exploit this concept for application in liposomal parenteral drug delivery vehicles, the inventor has designed a novel structural class of synthetic biocompatible amphiphiles. As additives to lipids for fabrication of liposomes, these synthetic amphiphiles are engineered as molecular devices for enhancing the stability and blood circulation half-life of liposomes as drug delivery vehicles.

Figure 1:
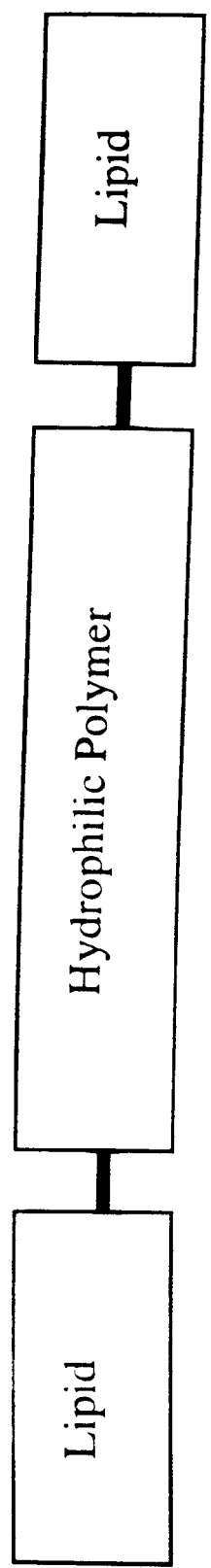
FIG. 1. Schematic diagram of the most simple amphiphilic molecule of the invention.
Figure 2:
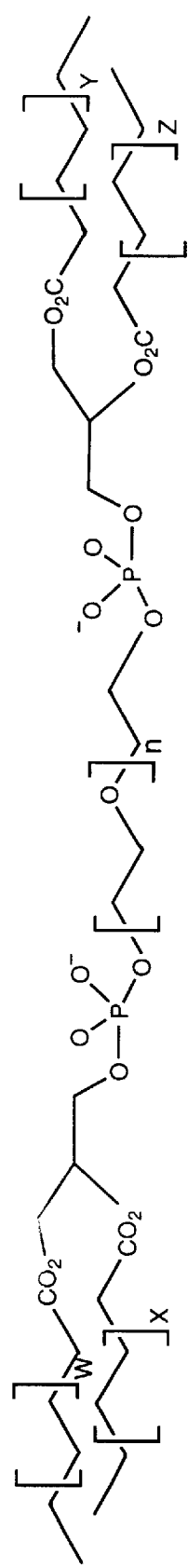
FIG. 2. Chemical representation of linear polyethyleneglycol conjugated to two terminal phospholipids. For DSPA-PEG(3350)-DSPA, W=X=Y=Z=16, n=75.
Figure 3:
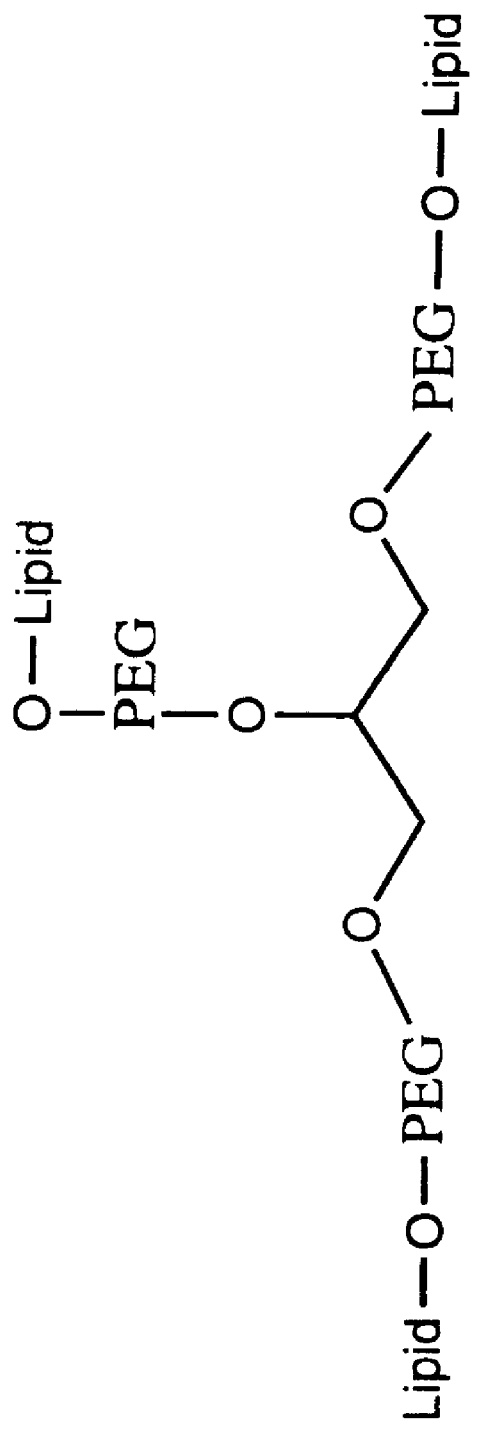
FIG. 3. A tripodal amphiphilic molecule containing PEGs (or other polymers) with glycerol or other polyol block inserts, attached to three lipids. For branched chain polymers or PEGs, all termini do not need to be conjugated with lipid provided the minimum bipodal criterion is fulfilled.
Figure 4:
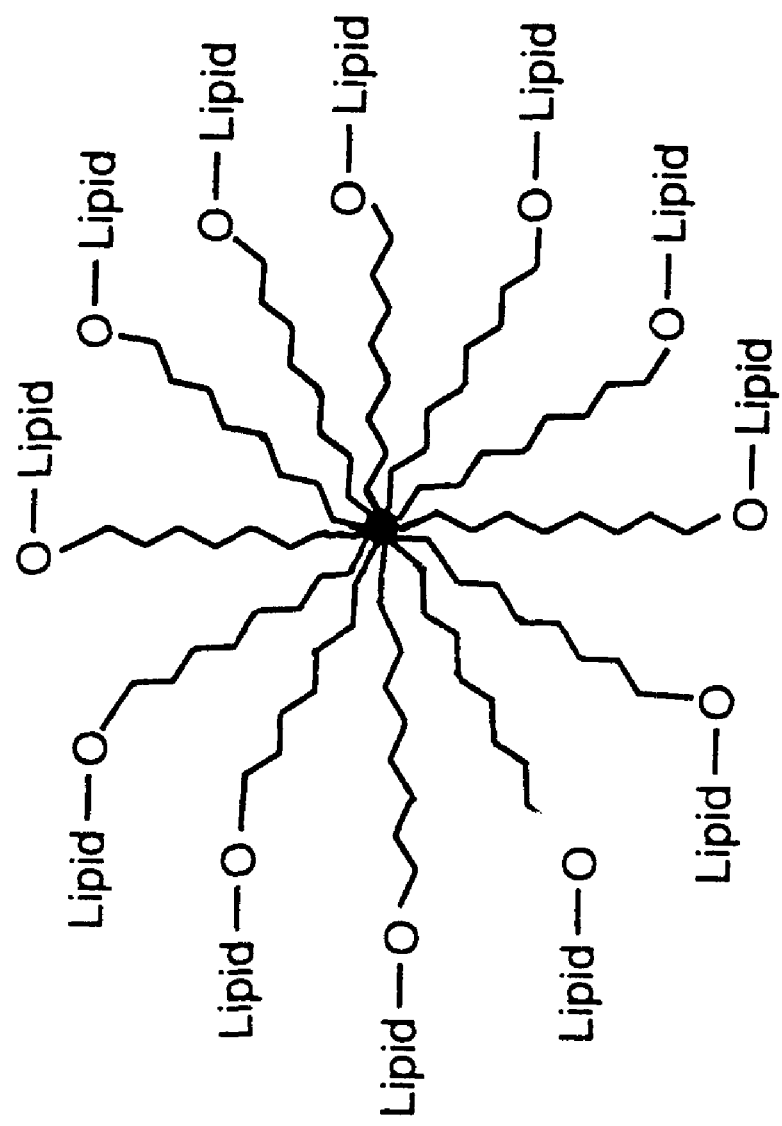
FIG. 4. A polypodal amphiphilic molecule derived from a star PEG or other polymer. For star PEGs, all termini may not be conjugated with lipid provided.

The salient features of the molecular design are embodied in FIG. 1, and further exemplified in FIG. 3, FIG. 4, FIG. 7, and FIG. 8. The generalized structure incorporates a hydrophilic biocompatible polymer residue which may have linear (FIG. 1), branched, pendant or star structure (for example, polyethylene glycols), covalently bridging and linking two or more terminal hydrophobic residues sterically compatible with the lamellar bilayer lipid (for example, phospholipids). The minimum required features are present in the linear polyethyleneglycol conjugated to two phospholipids as illustrated in FIG. 2. Although location of the multiple lipid residues at the termini of the polymer chains is illustrated, alternative locations along the polymer chains and at or near a single terminus are appropriate.

The novel structural class of amphiphiles of the claimed invention represents a radical departure from existing structural motifs. Additionally, this molecular design engenders enhanced bilayer stability and unique topography of the liposomal surface barrier. Together, these attributes will result in increases, and even dramatic increases, in liposome blood circulation half-life. The novel amphiphiles may also be employed as functional components of other types of drug delivery vehicles. In fact, the unique structural and physicochemical properties of the disclosed amphiphiles render them useful in various biomedical applications and for use as blood substitutes, parenteral nutritional fat emulsions, antigen-presenting vehicles in diagnostics, and in skin and other personal care consumer products.

A. Molecular Design of Bipodal and Polypodal Amphiphiles

The invention concerns, in part, the use of novel molecular devices for controlling the functions of non-covalent molecular aggregates and supramolecular assemblies such as liposomes. Molecular canopies, by analogy to their macroscopic counterparts, are visualized as extended molecular arrays and sheets of biopolymers positioned above the liposome surface and secured by multiple anchors or feet embedded in the outer lipid layer. These canopies cover the underlying finite lateral domains of the outer lamellar lipid layer and may be visualized also as multipronged molecular layer and clamps. At the functional level, the devices are akin to barrier guards and sentinels controlling traffic between lumen contents, the liposomal membrane, and the extraliposomal milieu. This physical conception at the molecular level has inspired the following molecular design.

Within this new molecular design, the hydrophilic compound will preferably be a biocompatible compound or polymer, and may have a linear, branched, pendant or star structure (see, e.g., Table 1). This hydrophilic compound or "hydrophile" is operatively attached to two or more hydrophobic moieties that are physically and geometrically compatible with lipid bilayers (see, e.g., Table 2). The hydrophobic moieties or "hydrophobes" are attached at spatially distinct, and preferably, at moderately or widely distant regions of the hydrophilic compound, including the termini of the hydrophilic compound.

In conventional amphiphile parlance, the PEG residue in the novel amphiphilic molecules is the head-group and the lipid part is the tail. Because the lipid residue in these amphiphiles is designed to serve as the footing for anchorage of the molecule on the liposomal surface, the inventor suggests the designation "pod" for it. Accordingly, the new class of molecules is designated as polypodal amphiphiles in which at least two lipid residues are linked at distinct, moderately or widely distant portions of, or at the termini of, linear or branched polyethyleneglycols or other hydrophilic polymers.

The simplest bipodal structural type is illustrated by the prototype structure α,ω-bisphosphatidyl-polyethyleneglycol (FIG. 2) (PA-PEG-PA). Other typical examples range from the tripodal (FIG. 3) containing branched PEG, to the polypodal (FIG. 4) derived from star PEGs. For branched chain and star PEGs, all termini may or may not be conjugated with lipid, provided the minimum bipodal criterion is fulfilled.

Figure 7:
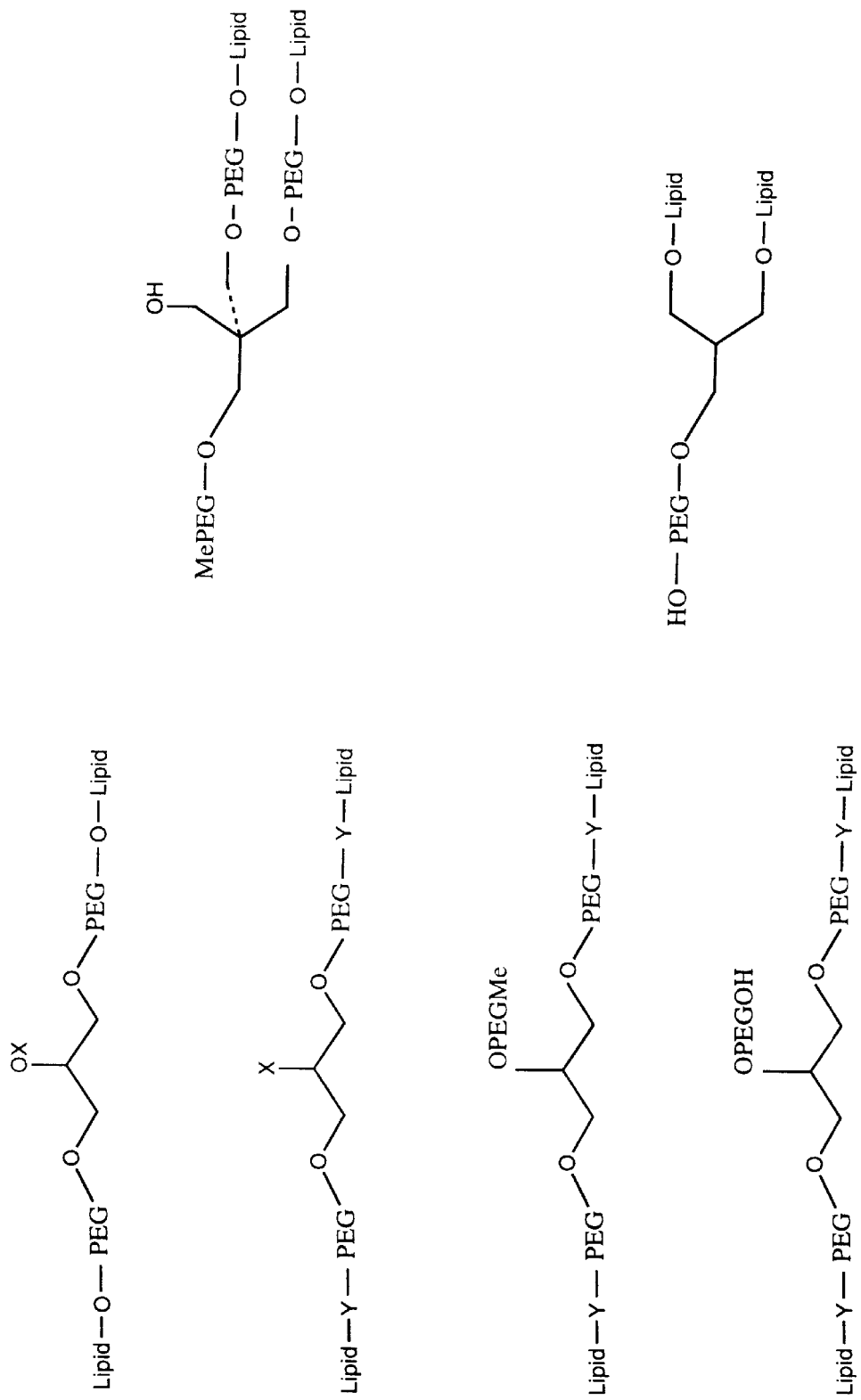
FIG. 7. Illustrative Biopodal Amphiphile Structures. Y=O, S, SS, NH, =N, HN(C=O), N-Alkyl, N,N-Dialkyl, N,N,N-Trialkylammonium, O(C=O), O(C=O)N, OP(=O)O$_2$, and equivalent bond types. X=Reactive residue or linker for conjugation to antigens, antibodies, biotin, chelators, receptor-mimics, and analogues.
Figure 8:
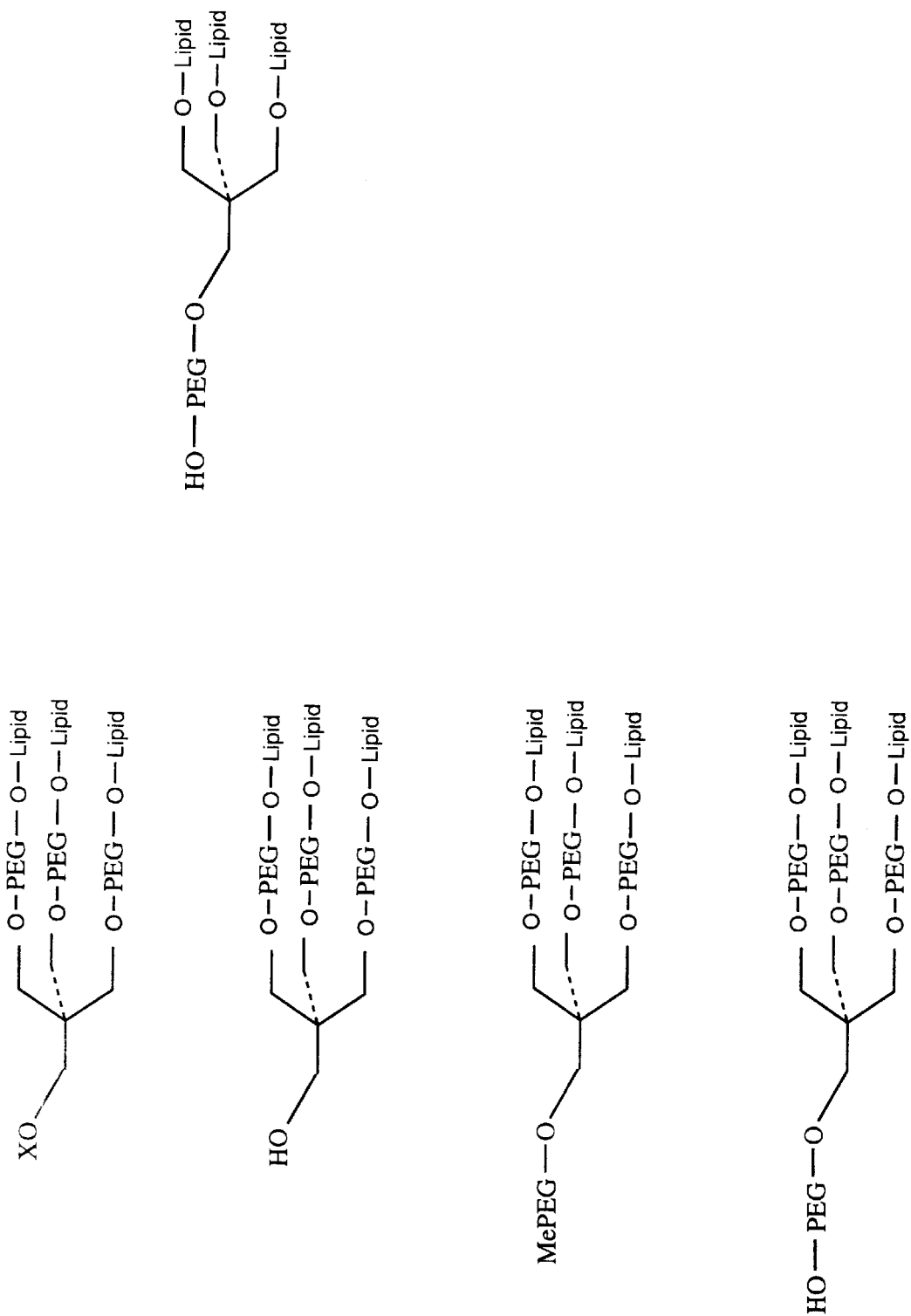
FIG. 8. Illustrative Tripodal Amphiphile Structures. X=Reactive residue or linker for conjugation to antigens, antibodies, biotin, chelators, receptor-mimics, and analogues.

Several illustrative structures are shown in FIG. 7 and FIG. 8. These incorporate glycerol or pentaerythritol residues either as polymer branching points for providing functional groups within the polymer residue, or for attaching multiple lipid residues. Branching or multiple functional groups within the polymer may be provided by polyols and their block polymers, by hydroxy- and amino acids and peptides. The functional groups may be attached directly or via linkers/spacer residues to antigens, antibodies and other pendant ligands.

The amphiphiles of the claimed invention contain lipophilic and hydrophilic structural components and as such are expected to be surface active. The properties depend inter alia on the relative balance of the hydrophilic PEG chains to the hydrophobic (lipophilic) lipid residues (HLB) (Griffin, 1949; 1954). Based on the knowledge that the monopodal types of the prior art, typified by MePEG-PE, are water soluble detergents and only form micelles in water at concentrations above the solubility limits (CMC), it could be rationally expected that the amphiphiles of the present invention may show identical behavior. Surprisingly, the inventor found that these amphiphiles show dramatically different behavior on interaction with water.

Specifically, the amphiphiles DOPA-PEG(2000)-DOPA, DOPA-PEG(3350)-DOPA, DSPA-PEG(3350)-DSPA and DSPA-PEG(8000)-DSPA, which exemplify the amphiphiles of the invention all form liquid-crystalline multimolecular aggregates. The mesophases characterized by X-ray diffraction include the fluid $L_\alpha$ and gel $L_\beta$, phases. This behavior is useful indeed because these phases, in excess water and on input of (sonic) energy, generate liposomes. It is emphasized that the prior art monopodal (using the new terminology) types MePEG(2000)-PE and MePEG(5000)-PE that are comparable in PEG polymer chain length or HLB, only form micelles in water. In particular, the monopodal materials of the prior art do not form liquid-crystalline phases as evidenced by the complete absence of X-ray diffraction patterns (Kenworthy et al., 1995a, 1995b; Needham et al., 1992; Lasic et al., 1991).

B. Components for use in Bipodal and Polypodal Amphiphiles

For preparing the amphiphilic molecules of the present invention, a variety of hydrophilic compounds and polymers, and a range of hydrophobic moieties may be employed and linked using various operative means.

1. Hydrophilic Compounds

The constraints inherent in the overall molecular design for the polypodal amphiphiles dictate that the hydrophilic polymer component must contain or be derivatized to contain a minimum of two functional groups suitable for attachment, or conjugation, to the lipid residues.

Apart from PEG introduced above, novel amphiphile structures may be based on hydrophilic polyvinylpyrrolidone, polyethleneimine, polylactic acid, polypeptide and related materials exemplified in Table 1. To be adequately hydrophilic, the materials should have measurable solubility in water, preferably greater than 10%, and also be soluble in organic solvents, such as chloroform, for facile handling during chemical conjugation to lipids and purification of the amphiphiles. Additional criteria for selection are based on the hydrophilic-lipophilic balance (HLB) desired in the derived novel amphiphile. Useful variations in structure, particularly in functional groups for conjugation to lipids and other pendant ligands, are particularly illustrated by reference to the case of PEGs. However, those of skill in the art will appreciate the application of this guidance to preparing a range of suitable polymers based on the types of compounds shown in Table 1.

TABLE 1

Structures Providing Hydrophilic Residues for Novel Amphiphiles

Polyethyleneglycols
Polyamine
Polyvinylpyrrolidone
Polyvinylmethylether
Polyhydroxypropylmethacrylate
Polyhydroxylpropylmethacrylamide
Polyhydroxyethyl acrylate
Polymethacrylamide TABLE 1-continued Structures Providing Hydrophilic Residues for Novel Amphiphiles Polydimethylacrylamide
Polymethyloxazoline
Polyethyloxazoline
Polyhydroxyethyloxazoline
Polyhydroxypropyloxazoline
Polyaspartamide polymer
Polyethyleneimine
Polylactic acid
Polypeptide and related materials
Polysulfone
Co-polymers of the monomers corresponding to the above
Oligomeric ethylene glycols
Polysorbates
Polycationic polypeptides PEG-diol and its derivatives wherein the terminal —OH groups have been replaced by other functional groups such as aldehyde alkylamine, diakylamine, trialkylamine, thiol, amino, carboxyl, and polyol are appropriate. The degree of polymerization (DP) of the ethylene glycol may vary widely. Depending on the desired physical attributes and applications, DP up to about 100, 200, 300, 400 and up to and even beyond about 500 are envisaged. For the linear, branched and pendant PEG types, this DP range corresponds to mol. wt. between about 100 (106.1 for diethylene glycol) to 10,1000 daltons (the units are omitted from the text henceforth). For star PEGs, molecular weights. approach 1,000,000. Other compounds and polymers of a similar molecular weight range are contemplated for use in the invention.

The linear PEGs are available readily from several commercial sources. Branched 3–8 arm PEGs with mol. wt. range 2000–20,000, prepared by ethoxylation of various polyols derived from glycerol condensation products, and star PEGs prepared from cross-linked divinylbenzene derivatives, are available from specialist suppliers (e.g., Shearwater Polymers, Inc., Huntsville, Ala.).

Figure 6:
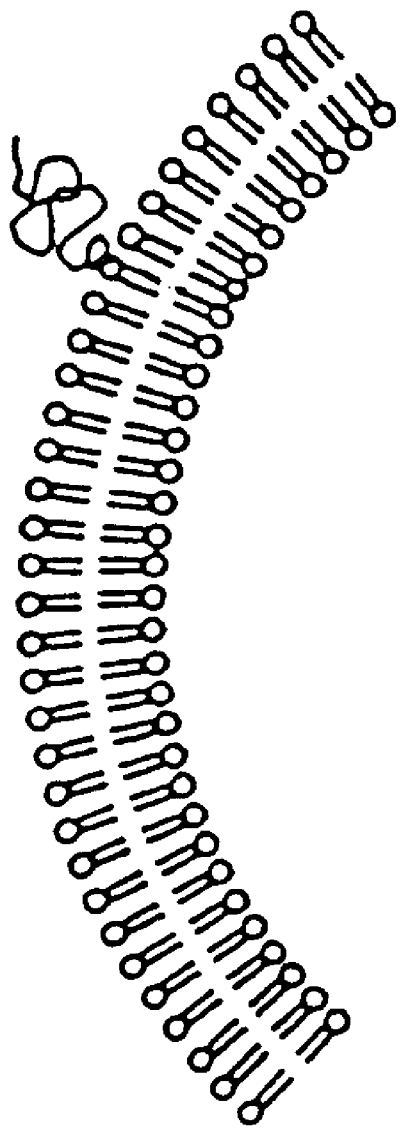
FIG. 6. Schematic representation of the likely topography of the MePEG chain of the monopodal MePEG-PE (Hristova and Needham, 1993) for contrast with the extended amphiphilic structures of the invention shown in FIG. 5.

Polymers incorporated into the structures illustrated in FIG. 6 and FIG. 7, are prepared by a nucleophilic substitution reaction of the bis- or polykis-methanesulfonyl esters-of the polyols with a very large excess of an ethylene glycol oligomer or a linear PEG by heating in the presence of a strong base, usually KOH or NaH. Preferably, prior to nucleophilic reaction, selected hydroxyl(s) in the polyol are blocked using benzyl ether type temporary protecting groups. The resulting products are freed from excess ethylene glycol or linear PEGs by fractional distillation or solvent partition between water and a water-immiscible organic solvent such as toluene. MePEG residues as branches or pendant spacer residues with (temporary protected) functional groups are introduced by analogous nucleophilic substitution reactions. The temporary protecting groups are removed, for instance the benzyl groups by catalytic hydrogenolysis, after conjugation to the lipids.

For certain applications, for instance in transfection and gene delivery vehicles, oligomeric or polymeric residues such as spermidine, spermine, polylysine, and related polyamine, polyethyleneamine, and polycationic materials are useful. Polypeptide residues are useful as mimics for cell membrane anchored receptors, and as antigens in diagnostics, and polyamino/cationic peptides for lung-surfactant replacement.

2. Hydrophobic Moieties

The lipid appendage must have proclivity for embedding in the bilayer without perturbing the geometrical packing and structure of the liquid crystalline phase. Molecules meeting these constraints may be selected from a wide variety of agents, including the nonionic, anionic and cationic residues commonly encountered in diacylglycerolipids, phospholipids, sphingolipids, and the synthetic cationic lipids Several useful examples are provided in Table 2 and this aspect of the invention is further illustrated by the anionic phosphatidate residues in the prototype structure of FIG. 2.

TABLE 2

Structures Providing Lipid/Hydrophobic Residues for Novel Amphiphiles

Alkyl/Alkenyl Ethers

Alkanol, primary or secondary
Alkanal (alkylaldehyde)
Methyl-alkyl ketones
Cationics/Polyamine Types N-Alkylamine
N-Methyl-N-alkylamine
N,N-Dimethyl-N-alkylamine
Acids/Amides/Esters Fatty acid
Monoalky phosphate (Monoalkylphosphoric acid)
Glyceride (Glycerol Fattyacid Esters/Ethers)

Monoglyceride (Mono-fattyacylglycerol)
Monoalkylglycerol
Diglyceride (Difattyacylglycerol)
Monoalkyl-monofattyacylglycerol
Deoxy-amino analogues of the above
Deoxy-N-methylamino analogues of the above
Deoxy-N,N-dimethylamino analogues of the above
Deoxy-N-N-dimethyl-N-alkylammonium analogues of the above
Glycosyl diglycerides
Sphingolipids Ceramidophosphoric acid
O-Acetyl-ceramidophosphoric acid
O-Fattyacyl-ceramidophosphoric acid
Ceramidophospho (in place of phospahtidyl) analogues of phospholipids
O-Acetyl-ceramidophospho (in place of phospahtidyl) analogues of phospholipids
O-Fattyacyl-ceramidophospho (in place of phospahtidyl) analogues of phospholipids
Phospholipids Diacylglycerophosphoric acid (Phosphatidic acid, PA)
Diacylglycerophospho-ethanolamine (Phosphatidylethanolamine, PE)
Diacylglycerophospho-N-methylethanolamine (NMePE)
Diacylglycerophospho--N,N-dimethylethanolamine (NMe$_2$PE)
Diacylglycerophospho-glycerol (Phosphatidylglycerol, PG)
Bis-diacylglycerophospho-glycerol (Bis-phosphatidylglycerol, BPG)
Diacylglycerophospho-inositol (Phosphatidylinositol, PI)
Phosphatidylinositol phosphates (PIP, PIP$_2$, PIP$_3$)
Phosphatidylinositol glycosides (Gly-PI)
Diacylglycerophospho-serine (Phosphatidylserine, PS)
Diacylglycerophospho-inositol (Phosphatidylinositol, PI)
Monoacyl analogues of the above (Lyso phospholipids)
Monoalkyl analogues of the above (Lyso phospholipids)
Monoacyl-monoaklyl analogues of above
Dialkyl/Alkylmethyl analogues of the above
Polyprenoid ether analogues of above
Polyol Derivatives Linear and branched polyglycerol-based analogues of glycero-, phospho-, sphingo-lipids
Polyol analogues of the above
Steroids Cholesterol
Phytosterols
Cholestanic acids
Cholesterol sulphate
Cholesterol succinate TABLE 2-continued Structures Providing Lipid/Hydrophobic Residues for Novel Amphiphiles Cholesterol phosphate
Cholesteryl phosphocholine
Labelled Compounds Analogues of all of the above with perfluoro-alkyl or perfluoro-fattyacyl residues
Analogues of all of the above with stable or radio-isotope labels including isotopes of C, H, F, N, O, P
Analogues of all of the above with fluoroscent, spin, biotin, thio-gold, investigational probe labels Structural variations commonly encountered in the diacylglycerol part of the lipid residue may be made; thus, the fatty chains may be identical or non-identical (mixed chain), and the chain type may vary in carbon length from short (where, preferably, multiple short chains are used), to medium (of about 8 C or so) to long (up to of about 26 C or even higher), and may be saturated or unsaturated. Other types of lipids, such as cholesterol, which close pack in lipid lamellar layers may be utilized as well.

It is stressed that in addition to the diacylglycerol based and analogous lipids which are characterized by two fatty chains attached to a glycerol residue, single fatty chain type alkyl ether, alkyl ester, alkylphosphate, alkylamine, dialkylamine, trialkylamine and related lipid types are appropriate as well because it has been determined in the present invention that the derived novel amphiphiles form mesophase on hydration. Further, multiple short (less than 8 C) lipid chains may be employed provided the overall HLB ensures self assembly into micelles or bilayers. Hydrophobic moieties such as fatty chains with alkyl, particularly methyl branches near the chain termini are appropriate as well.

Hydrophobic moieties such as fatty acids, phosphatidylcholines phosphatidylinositols and analogues, exemplified by the antineoplastic agents ET-18-OMe and hexadecylphosphocholine (Eibl and Unger, 1990), are contemplated to additionally provide beneficial biological activities to the derived novel amphiphiles.

Perfluoro analogues of the normal (hydrogen based) lipid moieties are appropriate for incorporating oxygen carrying capability into the novel amphiphiles. Preparations of novel amphiphiles with hydrophobic moieties carrying stable or radio-isotope labels including isotopes of C, H, F, N, O, P, or fluorescent, spin, biotin, thio-gold, and related labels are useful as investigational and diagnostic tools, particularly for establishing the metabolic fate of the novel amphiphiles.

C. Operative Attachment

Many types of covalent linkage are suitable for conjugating the PEG-polyol and lipid residues. The terminal —OH groups in PEG-polyols, or in normal terminal residues in most lipid types are not spontaneously reactive and must be activated for chemical reaction leading to conjugation. Derivatives such as methanesulphonate esters of alcohols serve as activated building blocks, for example in the reaction of 1,2-isopropylidene-glyceryl-3-methanesulphonate and linear PEG (diol) in the presence of NaH, and acid catalyzed hydrolysis to remove the isopropylidene group, for the synthesis of PEG ethers with two terminal (propane) diol residues. Subsequent conjugation with lipid generates a tetrapodal novel amphiphile structure.

The general strategy for synthesis is based on covalent conjugation of the appropriate preformed hydrophilic polymer and hydrophobic lipid, specifically PEG-diol and phosphatidic acid, by a one step condensation reaction. Methods for preparing lipids as well as single molecular species of PEGs with low to medium molecular weights have been developed and are available for adaptation to suit the novel molecular design. A general method for the conjugation of any alcohol with phosphatidic acid (Aneja et al., 1970; Aneja and Davies, 1970; Aneja, 1974; each incorporated herein by reference), is adaptable for the PEG-diol(3350) with distearoylphosphatidic acid (DSPA) as described herein, and for bipodals in general.

For the synthesis of fattyacyl esters the polymer is treated with a fattyacyl chloride in the presence of tert. amine base or equivalent acylating reagents.

Hydrophilic polymers with more than two hydroxyl groups may be utilized for the synthesis of the polypodal novel amphiphiles exactly as described for the bipodals. Synthesis as in EXAMPLE 1 through EXAMPLE 5 may be performed with an excess of the lipid to conjugate all hydroxyls, or alternatively, with a limited molar proportion of the lipid to generate a mixture of products with two or more lipid conjugands and one or more free hydroxyls. The latter are used as loci for attaching antigens, antibodies and like moieties, or additional pendant polymer residues, usually after replacement with more reactive residues such as thiol, or derivatization to an activated group, with or without a spacer or linker residue. The same type of chemistry is utilized also for linking the hydrophilic polymer to lipid moieties with intervening spacer residues.

Many covalent linkages are suitable for conjugating the hydrophilic polymer and lipid residues, including alkyl ether, acyl ester, phosphate ester, amide, azo-methine, carbamate, alkylamine, and alkylanimonium types.

It is noted that depending on the polymer, the lipid, and the bond type, the novel amphiphile may be non-ionic, charge neutral zwitterionic, (poly)anionic or (poly)cationic species. For the anionic and cationic species, the associated counter ions may be tailored, e.g. by ion exchange procedures. It is emphasized that the counter ion itself may be a cationic or anionic lipid.

Linear HO—(CH$_2$CH$_2$O)n—CH$_2$CH$_2$—OH (PEG-diol), and its branched, comb, and star polyol analogues are available in various molecular weights with low dispersity. Most are offered at adequately high purity appropriate for use in the proposed synthetic strategy. Similarly, phosphatidic acids with several fattyacyl types are available in high purity from commercial sources, including Nutrimed Biotech. The identity and purity of all starting materials is preferably to be verified by MALDI-TOF mass spectra, TLC/HPLC, and other appropriate analyses.

For in vivo applications in biomedicine, a linkage potentially metabolizable by non-specific chemical or enzymatic pathways is preferred. The phosphodiester linkage shown in the prototype structure (FIG. 2) and analogous PA-PEG-PA types selected for the present study meet such criteria. The corresponding bonds in conventional phospholipids, such as phosphatidylcholines are hydrolyzed in vitro by the phospholipase family of enzymes including phospholipases A$_2$, C, D, and lipases (phospholipase B) which collectively degrade the molecule inter alia into its simpler species. This metabolism makes phospholipids attractive as parenteral drug delivery vehicles. The metabolism of phosphatidylinositols (PI) occurs also via PI-specific and glycosyl-PI-specific phospholipase C families. In contrast, alkyl ether type linkages are relatively stable, particularly to hydrolytic enzymes, and are suited for oral administration, and for industrial applications.

D. Prototype Amphiphile: α, ω-Bisphosphatidyl-polyethyleneglvcol (PA-PEG-PA)

The method of preparation is illustrated by the synthesis of DSPA-PEG(3350)-DSPA (Aneja, 1997). Starting from 1,2-distearoyl-sn-glycero-3-phosphoric acid (distearoylphosphatidic acid, DSPA) and PEG-diol (av. mol. wt 3350), conjugation was carried out by the one step method for phosphatidylation of alcohols (Aneja et al., 1970; incorporated herein by reference). Reaction was carried out in pyridine serving as activating base and solvent, and 2,4,6-triisopropyl-benzenesulphonyl chloride as the phosphoryl activating agent. Reaction was started at room temperature, and then maintained at 45° C. for 3 h. Aqueous acid work-up, evaporation of pyridine under reduced pressure, and partition of the residue between hexane-methanol-dil HCl, and workup of the hexane layer yielded the crude reaction product.

In methods of purification and analysis, the optimum elution solvent composition was developed based on studies of $^1$H NMR line widths which changed from narrow in CDCl$_3$ to broad on addition of CD$_3$OD to very sharp in CDCl$_3$—CD$_3$OH—D$_2$O as solvents. The crude product is easily purified by liquid chromatography/HPLC on silica.

The final product was >99% pure by TLC, HPLC, and gel exclusion chromatography (GEC). It reacted readily with phenyldiazomethane to form a dibenzyl(phosphate) derivative. The $^1$H NMR clearly indicated the presence of four stearoyl chains (two DSPA residues) per PEG(3350) as required for DSPA-PEG(3350)-DSPA structure (FIG. 2). MALDI-TOF spectra of the product and its dibenzyl derivative, and molecular weight and polydispersity by GEC on PL-GEL columns using tetrahydroftiran as the mobile phase were all in accord with structure (FIG. 2).

This procedure for the preparation, purification, analysis and characterization of DSPA-PEG(3350)-DSPA is immediately applicable to all members of the PA-PEG-PA series, including DOPA-PEG(3350)-DOPA; DOPA-PEG(2000)-DOPA;. DSPA-PEG(8000)-DSPA.

E. Preparation of Liposomes

Amphiphilic lipids when dispersed in aqueous media form ordered liquid crystalline phases. Self organization is governed by the tendency of the hydrophilic parts of the molecules to remain in water and the nonpolar fatty parts to avoid water, and these tendencies force the hydrated molecules into thermodynamically stable states (lyotropic phases) depending on concentration, temperature, pressure, ionic strength, and pH. The aggregate structures include the various micellar and lamellar bilayer, and the non-equilibrium cubic phases.

The packing arrangements are dictated by the geometrical space requirements of the hydrated head groups and the fattyacyl hydrocarbon chains. The difattyacyl chain glycerophospholipids normally form lamellar bilayers. The crystal and the lyotropic phase structure and behavior of phospholipids, and methods for their study have been described in detail (Shipley, 1986; incorporated herein by reference). Lamellar bilayers above the hydrocarbon chain melting transition temperature (gel-to-liquid crystalline transition) on dilution with excess water and input of (mechanical) energy form the closed-end lamellar vesicles entrapping a part of the aqueous phase in the interior core forming liposomes. Liposomes may incorporate many bilayers (multilamellar; MLV)) or a single bilayer (unilamellar: ULV). The latter may be of small diameter and size (SUV) or relatively large (LUV) structures.

Several literature procedures are available for the preparation of liposomes (Navarro et al., 1985; incorporated herein by reference). The method based on hydration of solvent-free thin lipid films (Bangham and Horne, 1964; Szoka et al., 1980) is used for preparing MLVs. It is more convenient than the reversed-phase evaporation method. The latter often gives higher efficiency of entrapment, more homogeneous particle size distribution, and theoretically a greater capacity to capture solutes of large (Stokes) radius (Szoka and Papahadjopoulos, 1978), but these considerations are not critical for practicing the present invention. Unilamellar vesicles are prepared from MLVs by multiple freeze-thaw cycles followed by repeated extrusion through stacked 200 nm and 100 nm polycarbonate filters (Hope et al., 1985; Mayer et al., 1986). The procedures to be followed are outlined below.

1. Preparation of Multilamellar Vesicles

Appropriate molar proportions of conventional lipid (e.g., DSPC, DSPG, cholesterol) with or without an amphiphile of the invention are co-dissolved in chloroform, evaporated to dryness (by rotary evaporation, or in a stream of nitrogen) to a thin film, and kept under a high vacuum overnight to remove the last traces of volatiles. The dried lipid film is hydrated at a temperature just above the main phase transition temperature (at 65° C. for DSPC) with the selected aqueous phase (described below). The lipid film and the aqueous phase mixture are subjected to vortexing and controlled sonication in a bath-type ultrasonicator (Laboratory Supplies Company, NY). The resulting vesicular suspension is annealed (allowed to equilibrate) for several hours.

2. Preparation of Unilamellar Vesicles

Large unilamellar vesicles are prepared by further processing of the MLV prepared as described above. The MLV preparation is frozen and thawed many times to offset any potential tendency of the novel amphiphiles to promote fusion of vesicles, and then extruded 10 times through stacked 100 nm polycarbonate filters (Nucleopore) employing an extrusion device (Avestin, ON). The liposomes produced by extrusion techniques (LUVET) have been shown to be unilamellar and reasonably homogeneous with average diameters close to pore size of the filters employed, and to retain the aqueous phase contents of the MLVs (MacDonald etal., 1991).

3. Composition of the Aqueous Phase

The aqueous phase is normally saline, without or with phosphate or other buffers. Appropriate analyte, for instance calcein, and osmotic control polymer (polyvinylpyrrolidone, av. mol. wt. 40,000) may be predissolved as required.

4. Addition of Selected Agents

The novel structural class of amphiphiles of the claimed invention represents a radical departure from the existing structural motifs. Additionally, this molecular design engenders enhanced bilayer stability and unique topography of the liposomal surface barrier. Together, these attributes will result in increases, and even dramatic increase, in liposome blood circulation half-life. The novel amphiphiles may also be employed as functional components of other types of drug delivery vehicles. In fact, the unique structural and physicochemical properties of the disclosed amphiphiles render them useful in various biomedical applications and for use as blood substitutes, parenteral nutritional fat emulsions, antigen-presenting vehicles in diagnostics, and in skin and other personal care consumer products.

The gross topography of poly-anchored PEG residues seen in the case of MLVs prepared from the novel bipodal amphiphiles alone is seen also in MLVs based on mixtures of the novel bipodal amphiphiles with PCs. In the case of such lipid mixtures, little significant change in the lyotropic mesophase structure is observed over the complete composition range from about 5 mole percent to 80 mole percent novel amphiphile. Moreover, the same phase structure is obtained by vortex mixing of preformed MLVs prepared separately from the novel amphiphiles and PCs, as is produced in the conventional procedure wherein a thin film of intimately mixed lipid pair is hydrated.

Micelles are formed on hydration of novel amphiphiles designed with branched hydrophobic moieties bearing multiple lipid chains. Microemulsions are produced by homogenization of triglyceride oil and novel amphiphile in aqueous buffer. The novel orientation and topography of multiple PEG chains in novel liposomes is appropriate also for micelles and microemulsions, and indeed any lipid-bearing hydrophobic surface. The latter include the lipid bilayer membranes of biological cells. Thus a new cell surface is generated on treatment with novel amphiphile and comprises a poly-anchored PEG/polymer coat eclipsing the surface antigens. On the other hand, the poly-anchored PEG/polymer coat around a synthetic lipid assembly is most appropriate for attaching antigenic ligands for use in diagnostic test kits, and for supporting antibodies for targeting therapeutic liposomes to desired tissue cells.

F. Physicochemical Properties of Resultant Amphiphiles

The resultant amphiphiles are surface active. With comparatively large PEG chains as the hydrophilic head-group and two terminal phospholipid residues with long fattyacyls, the molecules may swell in water and show lyotropic mesomorphism to form liquid crystalline phases, by analogy with the behavior observed for simpler polar lipids (Small, 1986).

In conventional liposomes, whether multilamellar vesicles (MLV) or unilamellar vesicles (ULV), the hydrated lipid bilayers are present in the liquid-crystalline ($L_\alpha$) or the gel ($L_\beta$, $L_\beta$) phases at physiological temperature depending principally on the main chain melting transition ($T_c$) of the component lipids. The effect of polypodal amphiphiles as additional lipid components on the gross morphology and phase structure may be visualized as follows.

As a first approximation, the lipid ends in bipodal PA-PEG-PA with infinitely long PEG chain length may be regarded as two independent anionic phospholipids. This independence is indicated also by molecular models which suggest that long PEG chain permits a high level of flexibility and conformational mobility for the terminal lipid residues. Therefore, at low molar proportions, the anionic phospholipid residues of PA-PEG-PA will get incorporated into the bilayer as is observed with phosphatidylglycerol and analogous phosphatidyl-alkylester phospholipids. Such additives cause only a minimum of perturbation of the lyotropic phase of the lipid bilayer. Statistical mixing and the repulsive influence of the head group anionic charge promote wide separation between individuals. The morphology and effects of the PEG link between the terminal phospholipids spaced far apart in the lipid bilayer can then be considered.

For PA-PEG-PA, the repulsion between the anionic phosphate diester head groups prevents close approach of the terminal intramolecular lipid ends. At maximum separation, the PEG chain stretches as a zig zag parallel to the plane of the bilayer. At closest approach of the terminal lipids, the PEG chain may describe an inverted tear-drop. For the more probable intermediate distances separating the lipid ends, the PEG chains likely describe a semicircle as illustrated schematically for a single PA-PEG-PA chain in FIG. 5. This is contrasted with the currently held view of the topography of MePEG chain of the monopodal MePEG-PE shown schematically in FIG. 6.

The gross topography of the PEG multiple chains anchored in the lipid bilayer by terminal lipids of the polypodal branched and star type PEG-lipid conjugates can be visualized as a canopy held in place by multiple tethers to the terminal phospholipids acting as footings to secure the assembly. The canopy covers and secures the underlying finite lateral domain of the lamellar lipid layer and may be visualized also as multipronged molecular staple and clamp.

At a sufficient molar proportion and surface concentration of the novel amphiphile, multiple arrays of PEG chains may close pack, conceivably aided and strengthened by water bridges, and create a veritable continuum functioning as a barrier between the lipid bilayer and the surrounding medium.

Figure 5:
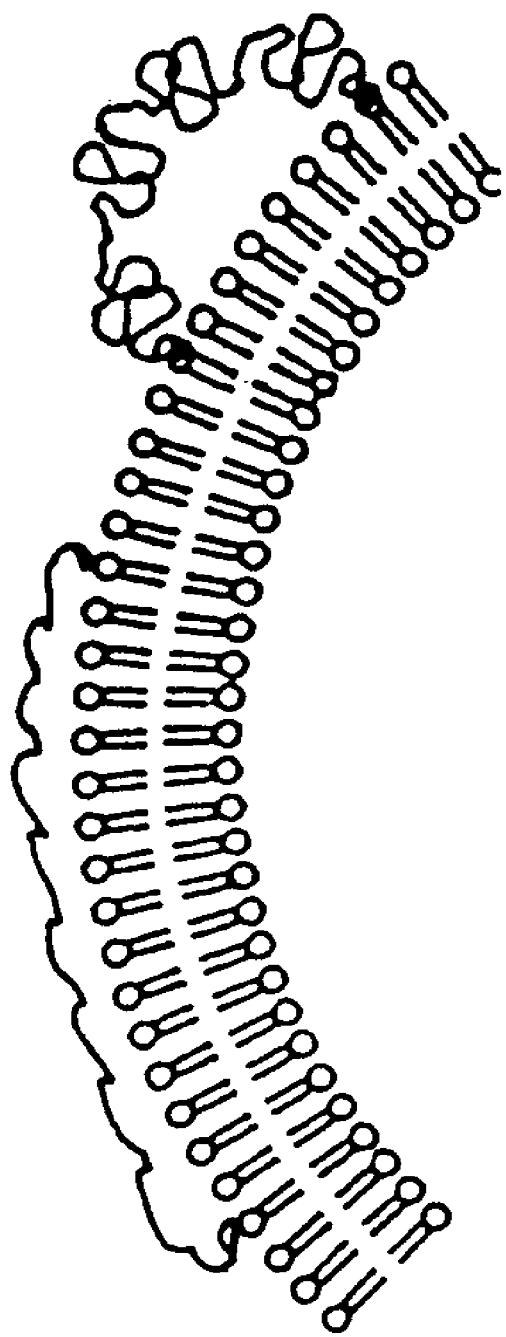
FIG. 5. Representative structures of amphiphilic molecules in liposome bilayers. At maximum separation, the polymer chain would stretch as a zig zag parallel to the plane of the bilayer (left). At intermediate distances separating the lipid ends, the polymer chains describe a semicircle as illustrated (right). For clarity only one polymer linked lipid is shown.

The proposed topography of FIG. 5 is unprecedented in synthetic lipid assemblies. However, similar molecular arrangements are known in natural membrane receptors such as the $\beta_2$-adrenergic receptor (Lefkowitz et al., 1983). Pairs of transmembrane spanning hydrophobic polypeptide regions may be likened to the terminal lipids of FIG. 2, jointly anchoring in the cytoplasmic or extracellular aqueous medium, one hydrophilic domain of polypeptide akin to the PEG chain in the doubly anchored lipid bilayer.

G. Analytical Techniques

Liposome preparations with and without the amphiphile additives of the invention are characterizable by the following techniques. Execution of these techniques ensure that preparations with the amphiphiles have the gross morphology, and, the underlying lipid bilayer structure and liquid crystal phase status required.

1. Size Determination of Liposomes

In comparative studies, the size distribution of liposomes prepared with and without the amphiphile additive is determined by HPLC gel exclusion chromatography on TSK-G6000 PW column (Lesieur et al., 1993) calibrated against a Coulter sub-micron particle size analyzer (Model 4N Plus) which employs Photon Correlation Spectroscopy.

2. Differential Scanning Calorimetry (DSC)

DSC measures the difference in heat flow into a sample compared with a standard or reference, and can easily detect endothermic lipid phase transitions. The technique is used routinely to determine the gel, liquid-crystalline status of lipids in liposomes. Selected liposome preparations are characterized by DSC using Seiko Oscillating Differential Scanning Calorimeter (DSC 220C).

3. Chemical Stability

The prototypical amphiphile described above is a relatively stable compound. Degradation by hydrolysis of one or more fatty or phosphate ester bonds may occur during processing and storage of derived liposomes. The structural types anticipated by such hydrolysis are prepared by syntheses to obtain reference materials for use in analytical methods for detecting such degradation, and appropriate TLC/HPLC methods are used.

4. X-Ray Diffraction of Multilamellar Lipid Preparations

Unoriented multilamellar fully hydrated lipid preparations in sealed glass capillaries held in a point collimated X-ray beam produce recordable "powder" diffraction patterns. The overall lamellar repeat period calculated from X-ray diffraction pattern comprises discernible double lipid chain thickness and interbilayer separation arising from the aqueous fluid in contact with the polar head groups. For osmotically stressed multilamellar preparations, the interbilayer separation decreases as a function of applied pressure and reaches a minimum approaching the closest contact for the head groups of the opposing phospholipids. This closest approach distance increases dramatically for lamellae incorporating small proportions of phospholipids with very bulky polar head-groups. The osmotic pressure can be applied by a large molecular weight polymer osmoticant dissolved in the aqueous phase used for hydration of the lipids. The method has been validated for SOPC-cholesterol (2:1) bilayers in 100 mM NaCl with added polyvinylpyrrolidone (PVP) of average molecular weight 40,000 (Needham et al., 1992).

In the multilamellar vesicles prepared from phospholipid compositions doped with the novel amphiphiles, the bulky head group residues are expected to reside in and enlarge (widen) the interbilayer gap. Therefore, in comparative studies on preparations with and without a selected amphiphile, the interbilayer repeat distances are measured. In addition, the effect of osmotic pressures, produced by 4% PVP (up to ca. $1.6 \times 10^5$ dyne/cm$^2$), is evaluated. Lipids are hydrated and equilibrated above the gel to liquid-crystal transition temperatures loaded and held in quartz capillary tubes in the X-ray beam (Caffrey, 1985).

The results of the X-ray diffraction study show that the hydrated novel amphiphiles examined all form liquid-crystalline multimolecular aggregates. In addition, hydrated mixtures of novel amphiphiles with the conventional liposome-forming phospholipids phosphatidylcholines (PCs) at 20° C. are in the desirable $L_\beta$ gel mesophase. The reflections from DOPA-PEG(2000)-DOPA, DOPA-PEG(3350)-DOPA, and Oleoyl-PEG(1500)-Oleoyl display hexagonal symmetry but mixtures of each of these novel amphiphiles with 1-stearoyl-2-oleoyl-sn-glycero-3-phosphocholine (SOPC) form the fluid mesophase identified as lamellar $L_\alpha$ Hydrated DSPA-PEG(3350)-DSPA and DSPA-PEG(8000)-DSPA alone and in mixtures with either SOPC or DSPC form mesophases characterized as the lamellar gel $L_\beta$, phase.

This behavior is particularly advantageous because the $L_\alpha$ and $L_\beta$ phases are MLVs, and in excess water and on input of (sonic) energy generate unilamellar liposomes. The previously available monopodal types MePEG(2000)-PE and MePEG(5000)-PE, that are comparable in PEG polymer chain length or HLB, only form micelles in water. These prior art 'monopodal' materials do not form liquid-crystalline phases as evidenced by the complete absence of X-ray diffraction patterns (Kenworthy et al., 1995a, 1995b; Needham et al., 1992; Lasic et al., 1991).

The repeat periods observed by X-ray diffraction and the calculated aqueous separation distance for the lamellar phases containing the novel amphiphiles are instructive. The data for DSPA-PEG(3350)-DSPA are representative of the novel amphiphile group. The unidimensional bilayer repeat distance $d_{100}$ for MLVs of fully hydrated DSPA-PEG(3350)-DSPA is 104.5 Å. As the $d_w$ for distearoyl fattyacyl based PC in $L_\beta$ phase at 20° C. is 47.0 Å, (Marsh, 1990), the calculated aqueous separation distance $d_w$, is 57.5 Å. This unprecedented large $d_w$ is attributed to the pace required by the hydrated PEG(3350) residue which must reside in the aqueous layer between apposed lipid bilayers.

The system SOPC plus DOPA-PEG(3350)-DOPA formed a mesophase identified as lamellar $L_\alpha$ with bilayer repeat period of 100.3 Å, and $d_w$ equal to 59.7 Å.

The system SOPC plus DSPA-PEG(3350)-DSPA formed mesophase identified as lamellar a ($L_\alpha$), with $d_{100}$=102.0 Å, and $d_w$=55 Å.

SOPC Plus DOPA-PEG(2000)-DOPA forms the lamellar $L_\alpha$ phase with $d_{100}$=83.8 Å, and $d_w$=43.1 Å. It is noteworthy that the DOPA-PEG(2000)-DOPA, which has fluid unsaturated fatty chains, forms a hexagonal mesophase but in combination with SOPC produces a lamellar phase with expanded aqueous separation layer.

Figure 9:
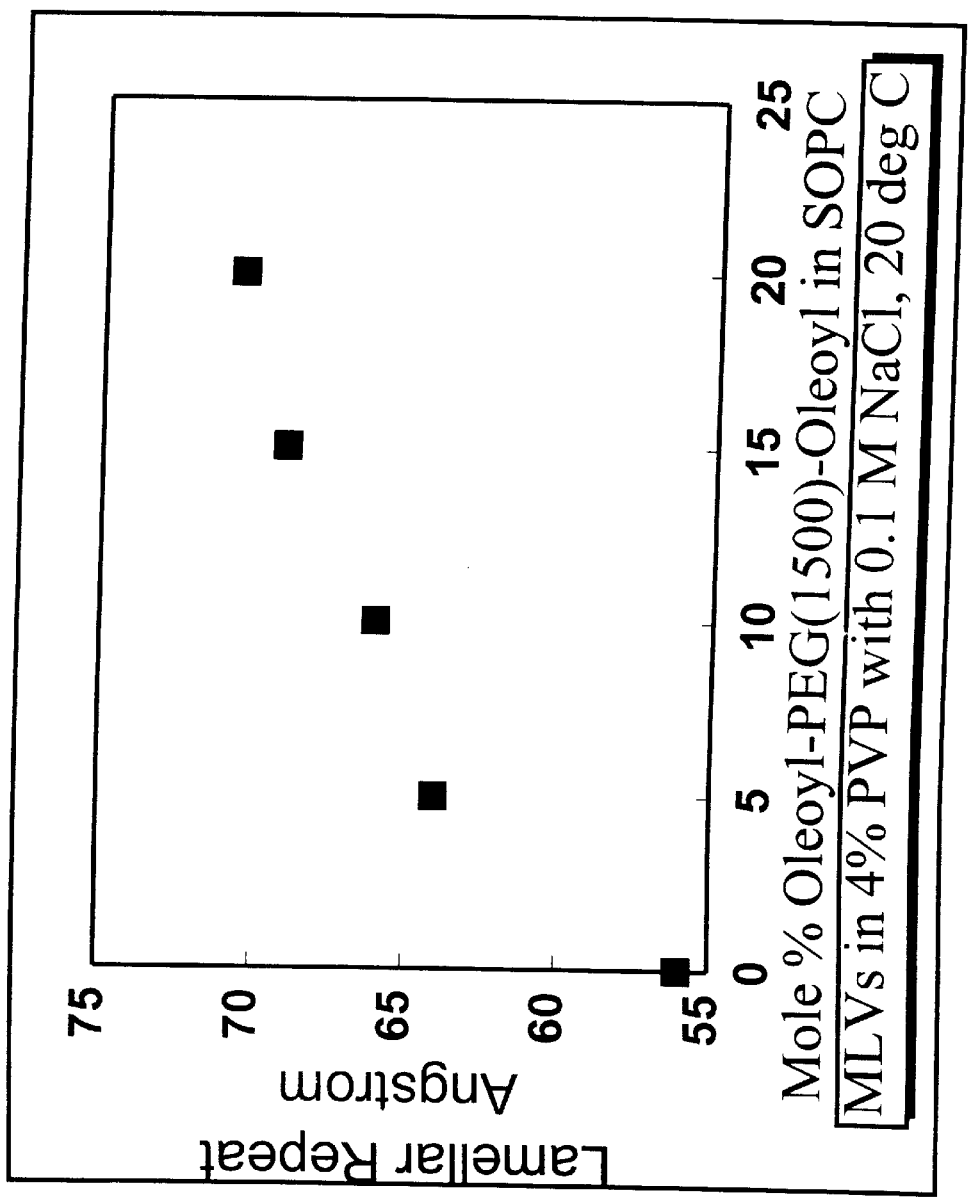
FIG. 9. Lamellar repeat period for Oleoyl-PEG (1500)-Oleoyl in SOPC as a function of mol % Oleoyl-PEG(1500)-Oleoyl at 20° C. and constant applied osmotic pressure (1.6×10$^5$ dyne/cm$^2$).

The above noted lamellar repeat and aqueous separation distances are unusually long compared with SOPC and DSPC at comparable hydration and temperature. The ionic charge of the novel amphiphiles may contribute to this even though the data were obtained at the ionic strength of 100 mmolar salt. No charge exists in the non-ionic novel amphiphile Oleoyl-PEG(1500)-Oleoyl. FIG. 9 shows that the lamellar repeat period for Oleoyl-PEG(1500)-Oleoyl in SOPC increases monotonically as a function of mole percent Oleoyl-PEG(1500)-Oleoyl at 20° C. and constant applied osmotic pressure ($1.6 \times 10^5$ dyne/cm$^2$). Compared to $d_{100}$ of pure SOPC (0 mole % additive) at 58 Å, the distance increases to 70.44 Å for 20 mole percent Oleoyl-PEG (1500)-Oleoyl.

At the relatively high ion strength and osmotic pressure employed in these measurements, the repeat periods represent the closest approach distance for the adjacent bilayers. Thus at closest approach, the aqueous gap with novel amphiphiles is considerably wider than for the conventional controls without the novel lipids. This is attributable to the bulky PEG residues in the aqueous layer as hypothesized and indicates the molecular canopy type morphology illustrated in FIG. 1.

H. Liposome Entrapped Agents

1. Selected Agents

The selected pharmacological agents in the following tables are provided by way of example only and are not intended, in any way, to provide an exhaustive list of the components for use herewith. In fact, there is little in the make up of a compound that would prevent productive association with the liposomes and lipid complexes of the claimed invention as the selected agent may functionally associate with the hydrophilic or hydrophobic regions thereof, or may distribute between the two. The present invention also includes combinations, or cocktails, of selected agents, including those of the same or different classes, each associated with the same liposome or complex, or each associated with a distinct liposomal component within a population of liposomes.

In one example, cholesterol is used as a water-insoluble fat-soluble drug. MLVs are prepared as described (EXAMPLE 9) from the novel amphiphile DOPA-PEG (3350)-DOPA and cholesterol (molar ratio 1:1) hydrated with 100 mmolar NaCl (100% hydration). X-ray diffraction of MLVs shows no reflections for undissolved crystalline cholesterol, and indicates solubilization of cholesterol by interdigitation in the lyotropic mesophase of DOPA-PEG (33500)-DOPA.

TABLE 3A

| Pharmacological Agents |
|---|
| Exemplary Antineoplastics |
| Adriamycin |
| Docetaxel |
| Hexadecylphosphocholine |
| Paclitaxel |
| ET-18-OMe |

TABLE 3A-continued

| Pharmacological Agents |
|---|
| Antibiotics/Antibacterials |
| Aminoglycosides |
| Amoxicillin |
| Ampicillin |
| Bacitractin |
| Beta-Lactams |
| Carbapenins |
| Cephalosporins |
| Chloromphenicol |
| Clindamycin |
| Erythromycin |
| Gentamicin |
| Minocycline |
| Monobactams |
| Neomycin |
| Penicillins |
| Rifampin |
| Streptomycin |
| Tetracyclines |
| Vancomycin |
| Anti-fungals |
| Amphotericin B |
| Clotrimazole |
| Flucytosine |
| Anti-virals |
| Acyclovir |
| AZT |
| Interferons |
| Enzymes |
| Superoxide dismutase |
| Arginase |
| Adenosine deaminase |
| Onconase |
| Proteins/Peptides |
| Hirudin |
| Calcitonins |
| Haemoglobin |
| Immunogenic peptides |
| Polycationic polypeptides |
| Hormones/Growth Factors |
| Oxytocin |
| Interleukins |
| CSFs |
| LFAs |
| Interferons |
| Immunoglobulins |
| Antibodies for Liposome Targeting |
| Antibody to p-glycoprotein |
| Nucleic Acid Delivery |
| Plasmid |
| Genes |
| Nucleic acid molecule, construct or vector |
| Therapeutic polynucleotides |
| Antisense |
| Sense |
| Anti-malarials |
| Amebicides |
| Anti-protozoal agents |
| Parasiticides |

TABLE 3B

FURTHER CHEMOTHERAPEUTIC AGENTS

| CLASS | TYPE OF AGENT | NONPROPRIETARY NAMES (OTHER NAMES) | DISEASE* |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, brest, ovary, lung, Wilms' tumor, cervix, testis, soft-tissue sarcomas |
| | | Melphalan (L-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethylenimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimidazolecarboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) | Breast, colon, stomach, pancreas, ovary, head and neck, urinary bladder, premalignant skin lesions (topical) |
| | | Floxuridine (fluorodeoxyuridine; FUdR) | |
| | | Cytarabine (cytosine arabinoside) | Acute granulocytic and acute lymphocytic leukemias |
| | Purine Analogs and Related Inhibitors | Mercaptopurine (6-mercaptopurine; 6-MP) | Acute lymphocytic, acute granulocytic and chronic granulocytic leukemias |
| | | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide Tertiposide | Testis, small-cell lung and other lung, breast, Hodgkin's disease, non-Hodgkin's lymphomas, acute granulocytic leukemia, Kaposi's sarcoma |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |

TABLE 3B-continued

FURTHER CHEMOTHERAPEUTIC AGENTS

| CLASS | TYPE OF AGENT | NONPROPRIETARY NAMES (OTHER NAMES) | DISEASE* |
|---|---|---|---|
| | | Bleomycin | Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitotane (o,p'-DDD) Aminoglutethimide | Adrenal cortex Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol (other preparations available) | Breast, prostate |
| | Antiestrogen | Tamoxifen | Breast |
| | Androgens | Testosterone propionate Fluoxymesterone (other preparations available) | Breast |
| | Antiandrogen | Flutamide | Prostate |
| | Gonadotropin-releasing hormone analog | Leuprolide | Prostate |

*Neoplasms are carcinomas unless otherwise indicated.

TABLE 4

Additional Selected Agents

Oxygen Carriers

Haemoglobin
Perfluorinated Lipid novel amphiphiles
Nutrient/Parenteral

Fat emulsions
Omega-3-glycerides
Fat soluble vitamins
Tocopherols
Contrasting Agents Gadolinium complexes
Barium meal
Antigen presenting vehicles (Novel amphiphiles with attached ligands)

Lectin
RGD

Immunogenic peptides

Interleukins
CSFs
LFAs
Interferons
Immunoglobulins

In another example, the water-insoluble antineoplastic drug paclitaxel is used. MLVs prepared from DSPA-PEG (3350)-DSPA and paclitaxel (molar ratios 95:5 and 90:10) hydrated with 100 mmolar NaCl (100% hydration) and comparative controls from DSPC plus paclitaxel are examined by X-ray diffraction. No reflections are seen for undissolved crystalline paclitaxel in DSPA-PEG(3350)-DSPA plus paclitaxel based novel liposomes (EXAMPLE 11). The two test compositions retained the $L_\beta$ mesophase structure but the lamellar repeat period was 97.7 Å, compared with 104.5 Å for the hydrated novel amphiphile DSPA-PEG (3350)-DSPA. Thus paclitaxel is solubilized in DSPA-PEG (3350)-DSPA liposomes and this causes little perturbation of the lyotropic mesophase of the novel amphiphile based MLVS. In contrast, in the control MLVs, reflections were seen clearly for crystalline paclitaxel, together with the reflections for hydrated DSPC.

2. In Vitro Analyses

In vitro assays capable of predicting in vivo pharmacokinetics and bio-availability of a drug can be useful in the early stages of the design and development of liposome-entrapped drug formulations (Gregoriadis, 1988; incorporated herein by reference). Measurement of drug released under simulated in vivo conditions from liposome-encapsulated drug preparations is a valuable comparative parameter. The converse measure of drug remaining encapsulated is regarded as an objective measure of stability, even though the concept of liposome stability is rather complex (Lasic, 1993; incorporated herein by reference).

As dilution occurs upon intravenous injection, in vitro dilution-induced release assays have been designed wherein the dilution is equivalent to that encountered upon systemic delivery to humans. Buffered saline rather than serum is employed in most early stage assays. Usually, a water soluble fluorescent dye is employed as model drug because accurate measurement at low release levels is easy by fluorescence analysis.

For the preparation of MLVs and LUVs as described above, the dye is dissolved in the aqueous phase employed for lipid hydration. Non-trapped dye is removed from the liposomal preparation by gel filtration. The dye-loaded liposomes are incubated in phosphate buffered saline (PBS) at various dilutions at 37° C. for the desired time. Samples are withdrawn at intervals, and if necessary, the concentration is adjusted by addition of PBS to obtain an appropriate concentration for analysis.

An in vitro dilution-induced release assay as described above has been shown to give good agreement between the release rates determined in vitro and the pharmacokinetics in humans for liposomes loaded with the antineoplastic drug doxorubicin (Amselem et al., 1993; incorporated herein by reference). In the present case, it is recommended that this doxorubicin assay be adapted for incorporation, release and analysis of calcein (Yatvin et al., 1987; Liu and Huang, 1988; Klibanov et al., 1990).

Calcein is easily determined by fluorescence assay. It is interesting also because it is useful for potential future extension of the study to liposome interaction with cells. At the relatively high concentrations in the liposomal lumen employed in these assays, calcein is self-quenching but is highly fluorescent at low concentrations formed on leakage into the surrounding buffer. The latter can be determined by fluorescence measurement in the presence of the liposome entrapped calcein. Total liposome associated (encapsulated) calcein is assayed after liberation by treatment with 0.1%–2% Triton X-100 to lyse the liposomes. Liposomes prepared with an amphiphile of the claimed invention should be compared with liposomes prepared without such an amphiphile.

The liposomes are prepared in aqueous medium containing the calcein, the free calcein is separated from the liposomes by size exclusion gel chromatography on Sephadex G-50. The calcein-loaded liposomal eluate is diluted with PBS and then incubated at 37° C. for defined periods, and samples assayed for calcein. The liposomal phospholipids (L), liposome-associated calcein ($C_L$), and free calcein ($C_F$) in the diluted system is quantified. Total calcein ($C_T$) in the initial liposomes is determined after lysis with 0.1% Triton X-100. Fluorescence is measured using an HP 1046A unit in the scan mode. Total phospholipids are determined based on phosphorus assay (Bartlett, 1959). If all calcein in the G-50 eluate is liposome-associated, $$\%\text{Release}=\{[(C_T/L)-(C_L/L)]/(C_T/L)\}\times 100.$$

In comparative tests, a significantly slower release is anticipated from liposomes with the amphiphiles of the invention than without. Amphiphiles are recommended to be first valuated at 1, 2, and 3 mole % of total bilayer lipids. Further evaluated using dilution with BS:fetal calf serum (3:1) in place of PBS alone is advised as a prelude to in vivo embodiments.

Figure 10:
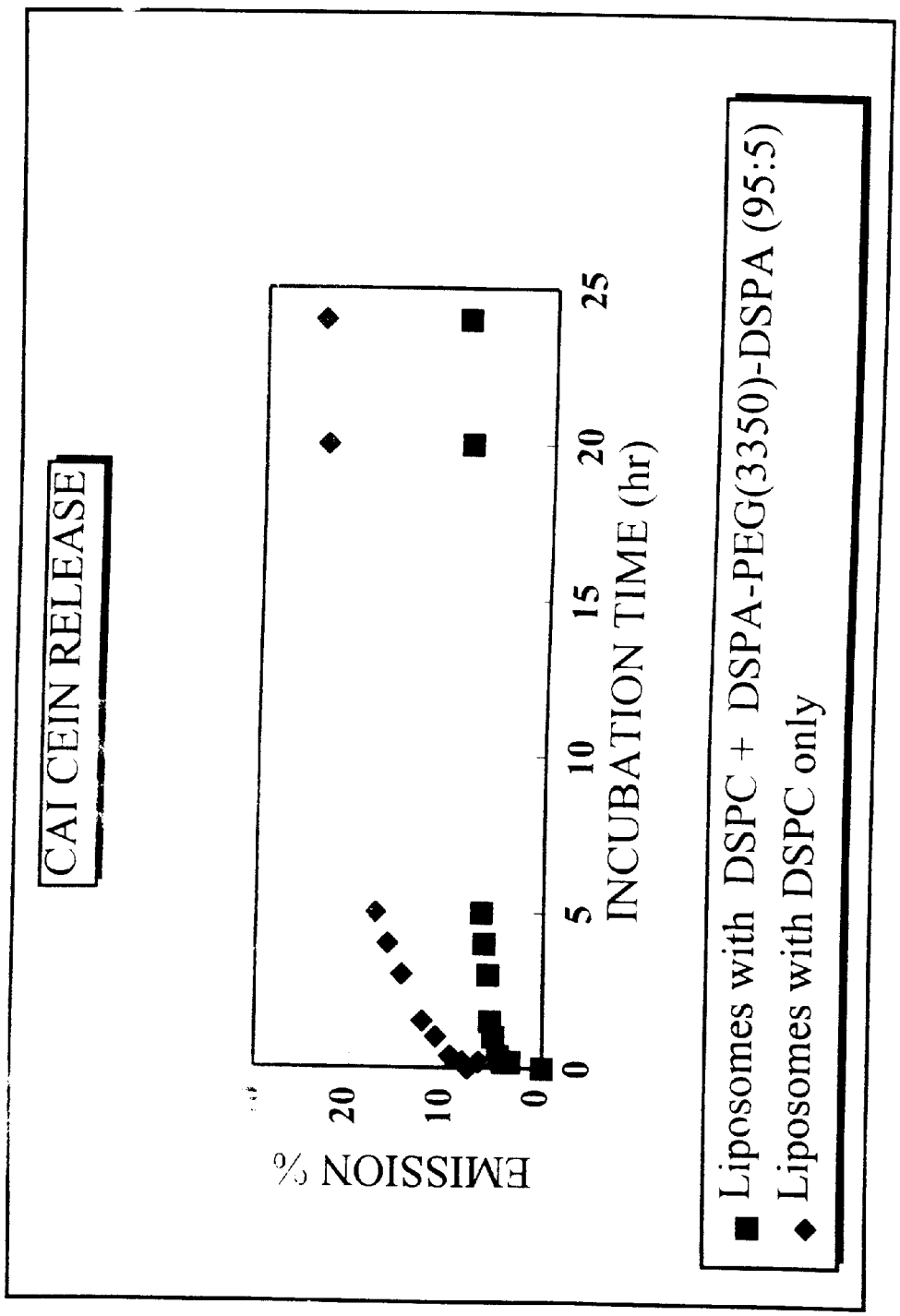
FIG. 10. Time course of release of calcein entrapped in liposomes based on DSCP plus DSPA-PEG(3350)-DSPA, and control liposomes based on DSPC only.

Novel liposomes (MLVs) with entrapped calcein as a water-soluble fluorescent drug model, prepared from a mixture (20 μmole) of DSPC and DSPA-PEG(3350)-DSPA (molar ratio 95:5) or from DSPC alone (control) in 0.025 M TRIS-HCl buffer at pH 7.4, were incubated with human serum. The time course of release of calcein, expressed as % emission at 520 nm, from novel and control liposomes is plotted in FIG. 10. The data show that the novel liposomes retain calcein more efficiently than control.

I. Liposome-Protein Interactions

Fluorophore labeled phospholipids are useful probes for investigating lateral, transverse, and intermembrane diffusion of lipids in synthetic vesicles and biological membranes. The 7-nitro-2-oxa-1,3-diazole (NBD) label in the fattyacyl residue has been applied widely (Chattopadhyay, 1990; Balch et al., 1994; Fattal et al., 1994; Nolan et al., 1995; each incorporated herein by reference).

1-Palmitoyl-2-NBD(hexanoyl)-sn-glycero-3-phosphocholine ($C_{16:0}$, $C_{6:0}$-NBD-PC) and related phospholipids with other common head groups are slightly water soluble but largely lipid bilayer resident in synthetic vesicles and in doped cell membranes. These probes are rapidly extracted from the bilayers by the addition of excess delipidated bovine serum albumin (Dao et al., 1991). This back-exchange requires intimate contact tantamount to penetration of BSA into the lipid outer layer. As the barrier effect for liposomes with added amphiphiles prevents such access, this method can be adapted for investigating interaction of BSA with LUVETs labeled with $C_{16:0}$, $C_{6:0}$-NBD-PC or with head group labeled dipalmitoyl-phosphatidyl-ethanolamine (NBD-PE). Following validation of this in vitro method for the interaction of LUVETs with extraliposomal proteins by appropriately stabilized reference LUVs, the method may be used as a measure relatable to proclivity for opsonization and uptake by the RES. For this validation, LUVETs (sterically) stabilized with MePEG(1900)-PE are employed as the reference liposomes.

The most promising formulation as per the dilution-induced release data are used to prepare LUVETs doped additionally with NBD-lipid at 1 mole % (the probes are available from commercial sources). LUVETs are treated with a large molar excess of BSA solution and incubated as described. The liposomes and BSA are separated by centrifugation and each assayed for NBD-lipid by fluorescence measurement (Dao et al., 1991).

J. Use in Cosmetics

Novel amphiphiles are applicable as conditioning agents in skin, hair and nail care products, providing moisturizing and lubrication attributes similar to endogenous ceramides.

Further applications are envisaged as cleansing agents in toothpastes, as self-emulsifying cream base for emollients, as oil absorbers for oily skin, and anti-gloss agents in lipid-based cosmetic formulations.

K. Use in Agriculture

Novel amphiphiles are appropriate for encapsulating pheromones for pest population estimates and control, and for other agricultural chemicals.

L. Use in Industry

Cationic as well as anionic type novel amphiphiles are useful as phase transfer agents in chemical catalysis. Other envisaged uses are: matrix for stabilizing enzymes in industrial biocatalytic processes, as lubricants in spinning acrylic and other synthetic fibers, as special emulsifiers, solubilizers and clarifiers.

M. Use in Medicine

Blood Substitutes

Novel amphiphiles with perfluoro lipid chains are considered superior to perfluorohydrocarbons as oxygen carriers in artificial blood substitutes. The potential advantages include low toxicity.

Alternative approaches involve encapsulation of hemoglobin in novel liposomes. This contrasts with the chemical conjugation of hemoglobin to MePEG in the prior art, which has not proven to be particularly successful.

Another novel approach involves the interaction between a red blood cell and novel liposome leading to non-covalently altered red blood cells supporting surface PEGs attached to the lipid residues anchored into the cell membrane lipid bilayer. The PEG canopies function to cover the cell surface receptors and to render these non-inimunogenic.

Lung Surfactant Replacer (for Respiratory Distress Syndrome)

No satisfactory product is currently available, but the present invention addressed this problem. For this application, the hydrophilic residue in the novel amphiphile is a polycationic moiety analogous to the polyaminopeptide sequence in lung surfactant protein.

Contrast Agents for MRI Imaging

As an example, novel amphiphiles conjugated with multidentate chelated Gadolinium ions will yield useful contrast agents for the GI tract.

Biomedical devices

Novel amphiphiles, particularly those with polyunsaturated (acetylenic) polymerizable lipid chains are applicable as surface coatings for biosurfaces, and reducing thrombogenicity of biomaterials.

Routes of Administration

The molecular design of novel amphiphiles allows much variation and consequently exact tailoring for route of administration. Accordingly, novel amphiphile-based vehicles are suitable for topical, inhalation, intradermal, intramuscular, intraperitoneal, and intravenous administration. All such pharmaceutical formulations are known to those of ordinary skill in the art and are further disclosed herein by virtue of incorporating by reference Remington's Pharmaceutical Sciences, 16th Ed. Mack Publishing Company, 1980.

Apart from liposomal-, micellar- and micro-emulsion type preparations, the novel amphiphiles may be used as a base for chewable tablets allowing gradual release of drug content.

Cancer Treatment

Liposomes are particularly appropriate vehicles for delivery of cytotoxic agents to the tumor tissue by passive targeting and by receptor-mediated specific targeting, as discussed. The data presented herein for paclitaxel shows that novel liposomes of the present invention are suitable encapsulating vehicles for this water insoluble drug, and by example for other water insoluble antineoplastics. The current formulation in polyethoxylated castor oil and ethanol causes serious adverse effects including general toxicity and allergic reactions in clinical use. These are expected to be alleviated by novel amphiphilic vehicle.

Nucleic Acid Delivery

Polycationic/polyamino ligands in novel amphiphiles are designed to facilitate incorporation of the polyanionic therapeutic genes and antisense nucleotides into liposomes. The surface PEGs prevent immunogenic reaction in intravenous and related parenteral administration. The protection offered by surface PEG coating in self-assembled novel lipid aggregates facilitates transport of entrapped biological agents in vivo to the target cells, including for transfection of tissues with therapeutic genes antisense nucleotides and ribozymes. Phosphatidylinositol-based lipid residues are particularly attractive because the lipid is cleavable by PI-specific phospholipases which are activated following receptor-mediated endocytosis of liposomes.

The following examples are included to demonstrate certain illustrative and preferred embodiments of the invention. It will be appreciated by those of skill in the art that the techniques disclosed in the examples that follow represent techniques discovered by the inventor to function well in the practice of the invention, and can thus be considered to constitute certain of the preferred modes for practicing various aspects of the invention. However, those skilled in the art will, in light of the present disclosure, also appreciate that many changes can be made in the particular embodiments that are disclosed herein and still obtain a like, similar or otherwise effective result without departing from the spirit and scope of the invention.

EXAMPLE 1

Preparation of α, ω-bis(1,2-Distearoyl-sn-glcero-3-phospho)-polyethylene-glycol(3350) [DSPA-PEG(3350)-DSPA]

Polyethyleneglycol, mol wt. 3350 (3.3500 g, 1.0 mmole) and 1,2-distearoyl-sn-glycero-3-phosphoric acid (distearoylphosphatidic acid, DSPA) (1.8149 g, 2.25 mmole) were dried under vacuum over $P_2O_5$, dissolved in anhydrous pyridine (15 ml) and treated with 2,4,6-triisopropyl-benzenesulphonyl chloride (TPSC1) (1.5143 g, 5.0 mmole) at R.T. for 30 min. followed by reaction at 45° C. for 2.5 hr. The procedure is adapted from the general method for phosphatidylation of alcohols (Aneja et al., 1970). The reaction mixture was cooled to 0–5° C. and treated with water (0.2 ml) for 18 hr. and then evaporated to dryness under reduced pressure at 37° C. The residue was applied to a column of flash chromatography silica packed in $CHCl_3$—$CH_3OH$—$NH_4OH$ (95:5:0.1), and eluted with the same solvent mixtures containing increasing proportions of $CH_3OH$ and $NH_4OH$. Pure title compound was eluted with $CHCl_3$—$CH_3OH$—$NH_4OH$ (93:75:0.3) and recovered by evaporation to dryness (3.7548 g, 79.65%).

The product, a colorless solid at R.T., was >99% pure by TLC on silicagel G eluted with $CHCl_3$—$CH_3OH$—$NH^4OH$ (85:15:2) (Rf 0.6), and HPLC on silicagel eluted with CHCl$_3$—CH$_3$OH—NH$_4$OH (89:10:1). It reacted readily with phenyldiazomethane (CAUTION, carcinogen and potential explosive) to form a dibenzylphosphate derivative (based on MS and NMR) that confirmed the bisphosphoric acid residue in the structure. MALDI-TOF MS 4730 (M+Na)$^+$, calcd. 4730. $^1$H-NMR (300 MHz, CDCl$_3$): δ ppm 0.87 (t, J 9.6, 12H, 4 CH$_3$), 1.34 (s, 104H, 52 CH$_2$), 1.60 (br, 8H, 4 CH$_2$), 2.0 (br, 8H, 4 CH$_2$), 2.58 (q. J 9.6 and 3.7, 8H, 4 CH$_2$), 3.64 (s, 302H, 75.5 OCH$_2$), 4.14, 4.38 and 4.41 (m, q. and dd, 8H, glycerol 4 CH$_2$O) 5.22 (m, 2H, glycerol 2 CH$_2$O), 7.15 (br, 2H, 2 P(=O)OH). The $^1$H NMR clearly indicated the presence of four stearoyl chains (two DSPA residues) per PEG(3350) as required for DSPA-PEG(3350)-DSPA structure 2.

DSPA-PEG(3350)-DSPA was examined by TG/DTA and DSC. The former showed weight loss of 1.7% below 100° C., and 3.6% loss below 170° C., DSC showed the main chain-melting endothermic transition at 51.9° C. with a premelting transition at about 33° C. In samples hydrated with 50% water, these shifted respectively to 50.5 and 35° C. The hydrated sample showed an additional endotherm at 115.9° C.

EXAMPLE 2

Preparation of α, ω-bis(1,2-Dioleoyl-sn-glycero-3-phospho)-polyethylene-glycol(3350) [DOPA-PEG(3350)-DOPA]

This compound was prepared from polyethyleneglycol, mol wt. 3350 (0.3350 g, 0.1 mmole) and 1,2-dioleoyl-sn-glycero-3-phosphoric acid (dioleoylphosphatidic acid, DOPA) (0,4431 g, 0.6 mmole), and characterized, exactly as described in Example 1 for DSPA-PEG(3350)-DSPA. The compound was obtained as a colorless glass at R.T., yield 0.3428 g (72.8%). The product was >99% pure by TLC on silicagel G eluted with CHCl$_3$—CH$_3$OH—NH$_4$OH (85:15:2) (Rf 0.6), and HPLC on silicagel eluted with CHCl$_3$—CH$_3$OH—NH$_4$OH (89:10:1). The $^1$H-NMR (300 MHz, CDCl$_3$) also showed δ ppm 5.34 (m, 8H, 4 HC=CH).

EXAMPLE 3

Preparation of α, ω-bis(1,2-Dioleoyl-sn-glycero-3-phospho)-polyethylene-glycol(2000) [DOPA-PEG(2000)-DOPA]

This compound was prepared from polyethyleneglycol, mol wt. 2000 (0.2000 g, 0.1 mmole) and 1,2-dioleoyl-sn-glycero-3-phosphoric acid (dioleoylphosphatidic acid, DOPA) (0.4332 g, 0.6 mmole), and characterized, exactly as described in Example 1 for DSPA-PEG(3350)-DSPA. The compound was obtained as a colorless glass at R.T. yield 0.2354 g (67.9%). The product was >99% pure by TLC on silicagel G eluted with CHCl$_3$—CH$_3$OH—NH$_4$OH (85:15:2) (Rf 0.7) and HPLC on silicagel eluted with CHCl$_3$—CH$_3$OH—NH$_4$OH (89:10:1). MALDI-TOF MS 3344 (M$^+$); the $^1$H-NMR (300 MHz, CDCl$_3$) also showed δ ppm 5.32 (m, 8H, 4 HC=CH).

EXAMPLE 4

Preparation of α, ω-bis(1,2-Distearoyl-sn-glycero-3-phospho)-polyethylene-glycol(8000) [DSPA-PEG(8000)-DSPA]

This compound was prepared from polyethyleneglycol, mol wt. 8000 (2.0000 g, 0.25 mmole) and 1,2-distearoyl-sn-glycero-3-phosphoric acid (distearoylphosphatidic acid, DSPA) (0.7259 g, 1.0 mmole), and characterized, exactly as described in Example 1 for DSPA-PEG(3350)-DSPA. The compound was obtained as a colorless solid at R.T., yield 1.88 g (80.0%). The product was >99% pure by TLC on silicagel G eluted with CHCl$_3$—CH$_3$OH—NH$_4$OH (85:15:2) (Rf 0.7), and HPLC on silicagel eluted with CHCl$_3$—CH$_3$OH—NH$_4$OH (89:10:1). MALDI-TOF MS 9590 (M$^+$); $^1$H-NMR (300 MHz, CDCl$_3$) was consistent with structure.

EXAMPLE 5

Preparation of α, ω-bis(Dioleoyl)-polyethylene-glycol(1500) [OLEOY-PEG(1500)-OLEOYL]

Polyethyleneglycol, mol wt. 1500 (1.6000 g. 1.07 mmole) was dried under vacuum over P$_2$O$_5$, dissolved in anhydrous pyridine (5 ml) and treated with oleoyl chloride (0.9629 g, 3.0 mmole) at 0–5° C. for 30 min. followed by reaction at R.T. for 16 hr. The reaction mixture was cooled to 0–5° C. and treated with water (0.5 ml) for 18 hr. and then evaporated to dryness under reduced pressure at 37° C. The residue was applied to a column of flash chromatography silica packed in CHCl$_3$—CH$_3$OH (99:1), and eluted with the same solvent mixtures containing increasing proportions of CH$_3$OH. Pure title compound was eluted with CHCl$_3$—CH$_3$OH (98.5:1.5) and recovered by evaporation to dryness (1.62 g, 75.0%).

The product, a colorless oil at R.T., was >99% pure by TLC on silicagel G eluted with CHCl$_3$—CH$_3$OH (95:5) (Rf 0.35), MALDI-TOF MS 2043 (M$^+$, calcd. 2040), 1774 (M—C$_{18}$H$_{33}$CO)$^+$, $^1$H-NMR (300 MHz, CDCl$_3$): δ ppm 0.86 (t, J 7.0, 6H, 2 CH$_3$), 1.26 (s, 36H, 18 CH$_2$), 1.58 (br, 4H, 2 CH$_2$), 1.97 (m, 4H, 2 CH$_2$), 2.30 (t, J 8.0, 4H, 2 CH$_2$C=), 3.63 (m, 132H, OCH$_2$), 4.20 (q, 4H, 2 HC=CH), 5.32 (m, 4H, 2 CH$_2$OCOOR).

EXAMPLE 6

Preparation of Unique Liposomes [Multilamellar Vesicles (MLVS) and Unilamellar Vesicles (ULVS)]

For the preparation of unique liposomes (liposomes with the amphiphiles of the invention), either as multilamellar vesicles (MLVs) or unilamellar vesicles (ULVs), in the first step the "classic thin film hydration" procedure (Bangham et al., 1965) was employed. A chloroform solution of the lipid, either novel amphiphile by itself e.g., DOPA-PEG(2000)-DOPA, or such an amphiphile in mixture with a phosphatidylcholine (PC) e.g., 1-stearoyl-2-oleoyl-sn-glycero-3-phosphocholine (SOPC) in selected mole % ratios, or such an amphiphile plus a PC plus cholesterol (CHOL), was evaporated to dryness to a thin film under a stream of N$_2$, the film was left under a high vacuum for at least 2 h, and hydrated above the main chain-melting transition (T$_c$) by treatment with a predetermined quantity (typically equal to lipid wt., noted as 100%) of water, aqueous buffer, salt, or polymer osmoticant solution.

The hydrates were equilibrated by vortex mixing, repeated cycles of freezing and thawing, and incubation above the T$_c$. Some of these preparations were examined in a polarized light microscope and these showed birefringence (myelin figures) characteristic of multilamellar bilayer structures (MLVs). The MLVs were stored at ambient temperature for 24 h. The liquid crystalline phase status of these hydrates was characterized by X-ray diffraction as described in EXAMPLES 7, 8 and 9. Dilution with additional quantity of the aqueous phase followed by sonication in bath sonicator (Laboratory Supplies Co., Hicksville, N.Y.) and/or extrusion of the MLVs through 100 μm pore diameter polycarbonate membranes (MacDonald et al., 1991) yielded ULVs. The ULVs were characterized and employed for encapsulation studies, e.g., of calcein as drug model in EXAMPLE 10.

EXAMPLE 7

Mesophases Formed by Hydrated Novel Amphiphiles

X-ray diffraction was used to characterize the liposomes (MLVs) prepared by hydration of the amphiphiles in EXAMPLE 6, specifically to define the mesophase structural type, and, for the lamellar bilayer phases, to measure the unidimensional bilayer repeat distance ($d_{100}$), and to calculate the aqueous separation distance ($d_w$) from the equation $d_{100}=d_w+d_1$, using the literature values for the lipid layer thickness ($d_1$) appropriate to the fattyacyl in the amphiphiles of the invention.

X-ray Diffraction Data Collection: All X-ray diffraction data were obtained at the D1 X-ray beam line at Cornell High Energy Synchrotron Source (CHESS). Fully hydrated lipids, prepared in EXAMPLE 6, in sealed thin-walled glass capillaries (dia. 1 mm) were held in a point collimated (0.3 mm) monochromatic (1.0 Å) X-ray beam. Wide- and low-angle powder diffraction patterns were recorded on X-ray sensitive Polaroid film. Sample temperature was controlled to±0.5° C. Exposure time varied from 15 sec to 10 min.

DOPA-PEG(2000)-DOPA: The wide-angle X-ray diffraction of fully hydrated DOPA-PEG(2000)-DOPA prepared with 100 minolar NaCl (100%) examined at 20.5° C. showed a single broad reflection at 4.52 Å corresponding to the short spacing of fluid phase. Low-angle reflections were observed at 75 Å (very strong, vs), 43.5 Å (medium, m) and 37.5 Å (weak, w) with the symmetry elements corresponding to the long spacings for a hexagonal mesophase.

DSPA-PEG(3350)-DSPA: The wide-angle X-ray diffraction of fully hydrated DSPA-PEG(3350)-DSPA prepared with 100 mmolar NaCl (100%) examined at 20.5° C. showed sharp reflections at 4.01 and 4.09 Å corresponding tot he short spacings of gel phase. Low-angle reflections were observed at 104.5 Å (strong, s), 52.3 Å (m) and 34.8 Å (w), that indexed clearly as first, second and third orders of a lamellar mesophase, identified based on the short spacing data as the lamellar β⁻ ($L_{β-}$) mesophase.

Thus, the unidimensional bilayer repeat distance $d_{100}$ for MLVs of fully hydrated DSPA-PEG(3350)-DSPA is 104.5 Å. As the $d_w$ for distearoyl fattyacyl based PC in $L_β$- phase at 20° C. is 47.0 Å (Marsh, 1990), the calculated aqueous separation distance $d_w$ is 57.5 Å. This unprecedented large $d_w$ is attributed to the pace required by the hydrated PEG (3350) residue which must reside in the aqueous layer between apposed lipid bilayers.

EXAMPLE 8

Mesophases Formed by Hydrated Novel Amphiphiles in Mixture With Phosphatidylcholines X-ray diffraction was used to characterize the liposomes (MLVs) prepared in EXAMPLE 1 by hydration of selected novel amphiphile and PC mixtures. The data define the mesophase structural type, and, for the lamellar bilayer phases, measure the unidimensional bilayer repeat distance ($d_{100}$) at a constant osmotic pressure, $1.6\times10^5$ dyne/cm² provided by 4% polyvinylpyrrolidone (PVP, mol. wt. 40,000, Sigma Chem. Co.) in 100 mmolar NaCl. Osmotic pressures for PVP solutions are recorded in the literature (Parsegian et al., 1986). The aqueous separation distance ($d_w$) is calculated from the equation $d_{100}=d_w+d_1$ using the literature values for lipid layer thickness $d_1$ appropriate to the fattyacyls in the novel amphiphile.

As in EXAMPLE 7, X-ray diffraction data was obtained at the D1 X-ray beam line at CHESS. Fully hydrated lipids in sealed thin-walled glass capillaries (dia. 1 mm) were held in a point collimated (0.3 mm) monochromatic (1.0 Å) X-ray beam. Wide- and low-angle powder diffraction patterns were recorded on X-ray sensitive Polaroid film. Sample temperature was controlled to±0.5° C. Exposure time varied from 15 sec to 10 min.

SOPC Plus DOPA-PEG(3350)-DOPA: The MLVs prepared from SOPC plus DOPA-PEG(3350)-DOPA (85:15 mol %) fully hydrated (100%) with 100 mmolar NaCl containing 4% PVP were examined at 20.5° C. Wide-angle X-ray diffraction showed a single broad reflection at 4.50 Å corresponding to the short spacing of fluid phase. Low-angle reflections were observed at 100.5 Å corresponding to the short spacing of fluid phase. Low-angle reflections were observed at 100.5 Å (s), 50.0 Å (m) and 33.5 Å (w), that indexed clearly as first, second and third orders of a lamellar mesophase. The mesophase is identified based on the short and long spacing data as lamellar α ($L_α$) with bilayer repeat period of 100.3 Å and $d_w$ equal to 59.7 Å.

SOPC Plus DOPA-PEG(2000)-DOPA: The MLVs prepared from SOPC plus DOPA-PEG(2000)-DOPA (3:1 mole ratio) fully hydrated (100%) with 100 mmolar NaCl containing 4% PVP at 20.1° C. gave data similar to that for DOPA-PEG(3350)-DOPA above. Low-angle reflections were observed at 83.8 Å (vs), 41.9 Å (s) and 27.9 Å (m), indicating a lainellar a ($L_α$) mesophase with $d_{100}$=83.8 Å, and $d_w$=43.1 Å.

It is noteworthy that the DOPA-PEG(2000)-DOPA, which has fluid unsaturated fatty chains, forms a hexagonal mesophase (EXAMPLE 7), but in combination with SOPC, produces a lamellar phase with expanded aqueous separation layer.

SOPC Plus DSPA-PEG(3350)-DSPA: The MLVs prepared from SOPC plus DSPA-PEG (3350)-DSPA (80:20 mole %) fully hydrated (100%) with 100 mmolar NaCl containing 4% PVP at 20.1° C. gave data similar to that for DOPA-PEG(3350)-DOPA above. Low-angle reflections were observed at 102.0 Å (strong, s) 51.0 Å (medium, m) and 34.0 Å (weak, w), that indexed clearly as first, second and third orders of a lamellar mesophase. The mesophase is identified based on the short and long spacing data as lamellar α ($L_α$), with $d_{100}$=102.0 Å, and $d_w$=55 Å.

EXAMPLE 9

Entrapment of Cholesterol in Hydrated Amphiphile

In this example, cholesterol was used as a water-insoluble, fat-soluble drug model. A solution of DOPA-PEG (3350)-DOPA and cholesterol (molar ratio 1:1) in chloroform was evaporated under nitrogen to a thin film and kept under a high vacuum for 2 h. The film was hydrated with 100 mmolar NaCl (100% hydration) at 30° C. and equilibrated at R.T. for 24 h. Low angle X-ray diffraction showed no reflections for undissolved crystalline cholesterol, and reflections at 83.8, 48.4, 43.45 and 31.71 Å, were at shorter distances compared with 100.0, 57.75, 50.0, and 38.0 Å for DOPA-PEG(3350)-DOPA alone in 100 mmolar NaCl, at 20.5° C. The shorter X-ray crystallographic distances indicate solubilization of cholesterol by interdigitation in the lyotropic mesophase of DOPA-PEG(33500)-DOPA with stretching of the PEG canopy and consequent shrinkage of the aqueous distance $d_w$.

EXAMPLE 10

Entrapment of Calcein in Hydrated Liposomes

In this example, calcein was used as a water-soluble fluorescent drug model. MLVs were prepared either from a mixture (20 μmole) of DSPC and DSPA-PEG(3350)-DSPA (molar ratio 95:5) or from DSPC alone (control) by the procedure given in EXAMPLE 6 except that the hydrating aqueous phase was 0.1 M solution of calcein in 0.025 M TRIS-HCl buffer at pH 7.4. After vortex mixing, more calcein in buffer (1 ml) was added and the mixture was sonicated in a water bath, initially at 55° C. and then at 40° C. until homogeneous. The slightly milky solution was extruded through a 100 nm pore size polycarbonate filter and passed through a Sephadex G-50 gel filtration column (1×15 cm) equilibrated in 0.025 M TRIS-HCl buffer at pH 7.4. Eluate fractions containing the extruded liposomes free from untrapped calcein were analyzed by thin layer chromatography and showed DSPC an DSPA-PEG(3350)-DSPA in approximately 95:5 molar ratio.

Aliquots (100 μl) of the liposomal eluate were incubated with 100 μl human serum (Sigma Chem. Co.) at 37° C. At timed intervals, 50 μl aliquots were diluted with TRIS buffer to 500 μl and the fluorescence emission at 520 nm was measured using excitation at 480 nm (Hewlett Packard 1046-A Fluorescence Detector. Fluorescence due to total entrapped calcein was measured by adding Triton X-100 (2% final concentration). The time course of calcein release expressed as % emission is plotted in FIG. 10. The data show that the novel liposomes retain calcein more efficiently than control.

EXAMPLE 11

Entrapment of Paclitaxel in Liposomes

The antineoplastic drug paclitaxel was used as an example of water-insoluble fat-soluble drug. Solutions of DSPA-PEG (3350)-DSPA and paclitaxel (molar ratios 95:5 and 90:10) in chloroform were evaporated under nitrogen to a thin film and kept under a high vacuum for 2 h. The film was hydrated with 100 mmolar NaCl (100% hydration) at 30° C. and equilibrated at R.T. for 24 h.

In comparative controls, liposomes were prepared from DSPC plus paclitaxel. Crystalline paclitaxel showed numerous strong reflections in wide and low angle X-ray diffraction at 20° C. The same reflections were seen clearly, together with the reflections for hydrated DSPC, and the DSPC plus paclitaxel controls. X-ray diffraction showed no reflections for undissolved crystalline paclitaxel in DSPA-PEG(3350)-DSPA plus paclitaxel based novel liposomes. The two test compositions retained the $L_\beta$- mesophase structure but the lamellar repeat period was 97.7 Å, compared with 104.5 Å for the hydrated novel amphiphile DSPA-PEG(3350)-DSPA. Thus paclitaxel is solubilized in DSPA-PEG(3350)-DSPA liposomes and this causes little perturbation of the lyotropic mesophase of the novel amphiphile based MLVs.

All of the compositions and methods disclosed and claimed herein can be made and executed by those of ordinary skill in the art without undue experimentation in light of the present disclosure. While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the claimed invention. More specifically, it will be apparent to those of ordinary skill in the art that certain agents that are chemically, structurally, functionally and/or physiologically related may be substituted for the particular agents described herein in order to yield the same, similar or otherwise beneficial results in accordance with the invention. All such similar substitutes and modifications apparent to those skilled in the art are to be included within the spirit, scope and concept of the invention as defined by the appended claims.

REFERENCES

The following references, to the extent that they provide exemplary procedural or other details supplementary to those set forth herein, are specifically incorporated herein by reference.

Allen and Chonn, *FEBS Lett.*, 223:4246, 1987.
Amselem, Cohen, Barenholz, *Chem. Phys. Lipids*, 64:219–237, 1993.
Aneja, *Biochem. Soc. Trans.*, 2:38–41:1974.
Aneja, Chadha, Davies, *Biochim. Biophys. Acta*, 218:102–111, 1970.
Aneja and Davies, *Chem. Phys. Lipids*, 4:60–71, 1970.
Aneja, "Symposium on drug delivery systems and drug formulation," ACS National Meeting, Apr. 12–17, San Francisco, Calif., Abstract, BIOT-003, 1997.
Bahr, Deppe, Karas, Hillenkamp, *Anal. Chem.*, 64:2866–2869, 1992.
Balch, Morris, Brooks, Sleight, *Chem. Phys. Lipids*, 70:205–212, 1994.
Bangham and Horne, *J. Mol. Biol.*, 8:660–668, 1964.
Bangham, Standish, Watkins, *J. Mol. Biol.*, 13:238–246, 1965.
Bartlett, *J. Biol. Chem.*, 234:466–468, 1959.
Beauchamp, Gonias, Menapace, Pizzo, *S.V Anal. Biochem.*, 131:25–33, 1983.
Caffrey and Bilderback, *Biochem. J.*, 45:627–631, 1984.
Caffrey, *Biochemistry*, 24:4826–4844, 1985.
Chattopadhyay, *Chem. Phys. Lipids*, 53:1–15, 1990.
Dao, McIntyre, Sleight, *Anal. Biochem.*, 196:46–53, 1991.
de Gennes, *Macromolecules*, 13:1069, 1980.
Delgado, Francis, Fisher, *Crit. Rev. Therap. Drug Carrier Syst.*, 9:249–304, 1992.
Dreborg and Akerblom, *Crit. Rev. Ther. Drug Carrier Syst.*, 6:315–365, 1990.
Fattal, Sholomo, Parente, Szoka, *Biochemistry*, 33:6721–6731, 1994.
Gombotz and Pettit, *Bioconjugate Chem.*, 6:332–351, 1995.
Gregoriadis, G., Ed., In: *Liposomes as Drug Carriers*, Wiley, N.Y., 1988.
Griffin, *J. Soc. Cosmet. Chem.*, 1:311, 1949.
Griffin, *J. Soc. Cosmet. Chem.*, 5:249, 1954.
Herbette et al., *Biophys. J.*, 20:245–272, 1977.
Hope, Bally, Webb, Cullis, *Biochim. Biochim. Biophys. Acta*, 812:55–65, 1985.
Hristova and Needham, In: *Stealth Liposomes*, Lasic D. and Martin, F., Eds. CRC Press, Boca Raton, pp. 35–49, 1993.
Inada, Matsushima, Kodera, Nishimura, *J. Bioact. Conpatible Polym.*, 5:343–364, 1990.
Katre, Adv. *Drug Delivery Rev.*, 10:91–114, 1993.
Kenworthy, Simon, McIntosh, *Biophys. J.*, 66 (Abstr.) A287, 1994.

Kenworthy, Simon, McIntosh, *Biophys. J.*, 68:1903–1920, 1995a.

Kenworthy, Hristova, Needham, McIntosh, *Biophys. J.*, 68:1903–1920, 1995b.

Klibanov, Maruyama, Torchilin, Huang, *FEBS Lett.*, 268:235–237, 1990.

Lasic, "Liposomes: From Physics to Applications," *Elsevier*, Amsterdam, 1993.

Lasic, Martin, Gabizon, Huang, Papahadjopoulos, *Biochim. Biophys. Acta*, 1070:187–192, 1991.

Lasic, Woodle, Martin, Valentincic, *Periodicum Biologorum*, 93(2):287–290, 1991.

Lasic and Barenholz, In: *Handbook of Nonmedical Applications of Liposomes*, Lasic, D. D. and Barenholz, Y., Eds. CRC Press, N.Y., Vol. IV, p. 308, 1996.

Lesieur, Madelmont, Paternostre, Ollivan, *Chem. Phys. Lipids*, 64:57–82, 1993.

Lefkowitz, Stadel, Caron, *Ann. Rev. Biochem.*, 52:159–186, 1983.

Liu and Huang, *Biochemistry*, 28:7700–7707, 1988.

MacDonald, MacDonald, Menco, Takeshita, Subbarao, Hu, *Biochim. Biophys. Acta*, 1061:297–303, 1991.

Marsh, CRC Handbook of Lipid Bilayers, CRC Press, Boca Raton, Fla., 168, 1990

Mayer, Hope, Cullis, *Biochim. Biophys. Acta*, 858:161–168, 1986.

McIntosh and Holloway, *Biochem.*, 26:7325–7332, 1987.

Mori, Klibanov, Torchilin, Huang, *FEBS Lett.*, 284:263, 1991.

Navarro, Chabot, Sherrill, Aneja, Zahler, Racker, *Biochemistry*, 24:4645–4650, 1985.

Needham, McIntosh, Lasic, *Biochim. Biophys. Acta*, 1108:4048, 1992.

Nishikawa, Arai, Inoue, *J. Biol. Chem.*, 265:5226, 1990.

Nolan, Magargee, Posner, Hammerstedt, *Biochemistry*, 34:3907–3915, 1995.

Parr, Ansell, Choi, Cullis, *Biochim. Biophys. Acta*, 1195:21–30, 1994.

Parsegian et al., *Methods Enzymol.*, 127:400–416, 1986.

Rand and Luzati, *Biophys. J.*, 8:125–137, 1968.

Sehon, *Adv. Drug Delivery Rev.*, 6:203–217, 1991.

Shannon, *Proc. Inst. Radio. Engrs.* N.Y., 37:10–21, 1949.

Shipley, In: *The Physical Chemistry of Lipids*, D. M. Small, Plenum Press, New York, 475–522, 1986.

Small, In: *The Physical Chemistry of Lipids*, Plenum Press, New York, 93, 1986.

Szoka, Olson, Heath, Vail, Mayhew, Papahadjopoulos, *Biochim. Biophys. Acta*, 601:559, 1980.

Szoka and Papahadjopoulos, *Proc. Natl. Acad. Sci. U.S.A.*, 7:4149, 1978.

Woodle and Lasic, *Biochim. Biophys. Acta*, 1113:171–199, 1992.

Woodle, Engbers, Zalipsky, *Bioconjugate Chem.*, 5:493496, 1994.

Woodle, Mathay, Newman, Hidayat, Collins, Redmann, Martin, Papahadjoupols, *Biochim. Biophys. Acta*, 1105:193, 1992.

Worthington, *Biophys. J.*, 9:222–234, 1969.

Yatvin, Tegmo-Larsson, Dennis, In: *Methods in Enzymology*, Academic Press, Inc., Vol. 149, p. 77–87, 1987.

Zalipsky, *Bioconjugate Chem.*, 6:150–165, 1995.

What is claimed is:

1. A kit comprising, in a suitable container, amphiphilic molecules comprising a hydrophilic component having at least a first and second terminus and at least a first and second hydrophobic moiety separately attached to, or proximal to, said first and second terminus; or a liposomal formulation comprising said amphiphilic molecules; wherein said kit further comprises a selected agent.

2. A cosmetic formulation comprising, in a cosmetically acceptable base, a population of liposomes or lipid complexes that comprise amphiphilic molecules that comprise a hydrophilic component positioned over at least a portion of the outer surface of the liposome or lipid complex; wherein said hydrophilic component has at least a first and second terminus and wherein at least a first and second hydrophobic moiety is separately attached to, or proximal to, said first and second terminus, said first and second hydrophobic moieties extending into the hydrophobic bilayer of the liposome or lipid complex.

3. A medicinal delivery composition comprising, in a pharmaceutically acceptable vehicle, a population of liposomes or lipid complexes comprising a selected agent; wherein said liposomes or lipid complexes comprise amphiphilic molecules that comprise a hydrophilic component positioned over at least a portion of the outer surface of the liposome or lipid complex; wherein said hydrophilic component has at least a first and second terminus and wherein at least a first and second hydrophobic moiety is separately attached to, or proximal to, said first and second terminus, said first and second hydrophobic moieties extending into the hydrophobic bilayer of the liposome or lipid complex.

4. A method for providing a selected agent to an animal, comprising administering to said animal a medicinal delivery composition comprising, in a pharmaceutically acceptable vehicle, a population of liposomes or lipid complexes comprising said selected agent; wherein said liposomes or lipid complexes comprise amphiphilic molecules that comprise a hydrophilic component positioned over at least a portion of the outer surface of the liposome or lipid complex; wherein said hydrophilic component has at least a first and second terminus and wherein at least a first and second hydrophobic moiety is separately attached to, or proximal to, said first and second terminus, said first and second hydrophobic moieties extending into the hydrophobic bilayer of the liposome or lipid complex.

5. The method of claim 4, wherein said selected agent is a nutrient or a nutritional supplement.

6. The method of claim 4, wherein said selected agent is an oxygen carrier, haemoglobin, a coagulant or a blood product.

7. The method of claim 4, wherein said selected agent is an antigen, an antibody, an immunological component, a cytokine or an anti-inflammatory agent.

8. The method of claim 4, wherein said selected agent is a chemotherapeutic agent or cytotoxin.

9. The method of claim 4, wherein said selected agent is a protein, peptide, enzyme, hormone, growth factor or neurotransmitter.

10. The method of claim 4, wherein said selected agent is an antibiotic, an anti-viral or a fungicide.

11. The method of claim 4, wherein said selected agent is an anaesthetic.

12. The method of claim 4, wherein said selected agent is nucleic acid molecules, a nucleic acid construct or vector, an antisense nucleic acid or a ribozyme.

13. The method of claim 4, wherein said animal is a human subject.

14. The method of claim 4, wherein said hydrophilic component of said amphiphilic molecules is a substantially linear, a branched, a pendant or a star hydrophilic component.

15. The method of claim 4, wherein said hydrophilic component of said amphiphilic molecules is a hydrophilic component from Table 1.

16. The method of claim 4, wherein at least one of said hydrophobic moieties of said amphiphilic molecules is a hydrophobic moiety from Table 2.

17. The method of claim 4, wherein said amphiphilic molecules are bipodal amphiphilic molecules comprising a substantially linear hydrophilic component that has a first and second terminus, and wherein a first and second hydrophobic moiety are separately attached at, or substantially at, said first and second terminus.

18. The method of claim 4, wherein said amphiphilic molecules are oligopodal or polypodal amphiphilic molecules comprising a branched or star hydrophilic component that has a plurality of termini and a plurality of hydrophobic moieties separately attached to each terminus or proximal thereto.

19. The method of claim 4, wherein said selected agent is an agent from Table 3A, Table 3B or Table 4.

20. The method of claim 4, wherein said selected agent is a surfactant.

21. A method for providing a selected agent to an animal, comprising administering to said animal a medicinal delivery composition comprising, in a pharmaceutically acceptable vehicle, a population of liquid-crystalline multimolecular aggregates comprising said selected agent; wherein said liquid-crystalline multimolecular aggregates comprising a plurality of amphiphilic molecules that comprise a hydrophilic component having covalently attached, at spatially distant sites, at least two hydrophobic moieties, wherein the mesophases of said liquid-crystalline multimolecular aggregates, as characterized by X-ray diffraction, include the fluid $L_\alpha$, gel $L_\beta$, and hexagonal mesophases.

22. The composition of claim 3, wherein said selected agent is a nutrient or a nutritional supplement.

23. The composition of claim 3, wherein said selected agent is a blood product.

24. The composition of claim 3, wherein said selected agent is an immunological component.

25. The composition of claim 3, wherein said selected agent is a chemotherapeutic agent or cytotoxin.

26. The composition of claim 3, wherein said selected agent is a protein, peptide, enzyme, hormone, growth factor or neurotransmitter.

27. The composition of claim 3, wherein said selected agent is an antibiotic, an anti-viral or a fungicide.

28. The composition of claim 3, wherein said selected agent is an anaesthetic.

29. The composition of claim 3, wherein said selected agent is nucleic acid molecules, a nucleic acid construct or vector, an antisense nucleic acid or a ribozyme.

30. The composition of claim 3, wherein said selected agent is a surfactant.

31. The composition of claim 3, wherein said selected agent is an agent from Table 3A, Table 3B or Table 4.

32. The composition of claim 3, wherein said hydrophilic component of said amphiphilic molecules is a substantially linear, a branched, a pendant or a star hydrophilic component.

33. The composition of claim 3, wherein said hydrophilic component of said amphiphilic molecules is a hydrophilic component from Table 1.

34. The composition of claim 3, wherein at least one of said hydrophobic moieties of said amphiphilic molecules is a hydrophobic moiety from Table 2.

35. The composition of claim 3, wherein said amphiphilic molecules are bipodal amphiphilic molecules comprising a substantially linear hydrophilic component that has a first and second terminus, and wherein a first and second hydrophobic moiety are separately attached at, or substantially at, said first and second terminus.

36. The composition of claim 3, wherein said amphiphilic molecules are oligopodal or polypodal amphiphilic molecules comprising a branched or star hydrophilic component that has a plurality of termini and a plurality of hydrophobic moieties separately attached to each terminus or proximal thereto.

37. The composition of claim 3, wherein said amphiphilic molecules comprise a plurality of hydrophobic moieties that extend into the hydrophobic bilayer of said liposome or lipid complex and wherein said hydrophilic component is positioned over a substantial portion of the outer surface of said liposome or lipid complex.

38. The kit of claim 3, wherein said selected agent is a pheromone or an agricultural agent.

39. A formulation comprising a population of liposomes or lipid complexes, wherein said liposomes or lipid complexes comprise amphiphilic molecules that comprise a hydrophilic component positioned over at least a portion of the outer surface of the liposome or lipid complex; wherein said hydrophilic component has at least a first and second terminus and wherein at least a first and second hydrophobic moiety is separately attached to, or proximal to, said first and second terminus, said first and second hydrophobic moieties extending into the hydrophobic bilayer of the liposome or lipid complex, and further comprising a selected agent.

40. The formulation of claim 39, wherein said formulation is a cosmetic formulation.

41. The formulation of claim 39, wherein said formulation is a medicinal delivery formulation.

42. A composition comprising a liquid-crystalline multimolecular aggregate comprising a selected agent; wherein said liquid-crystalline multimolecular aggregate comprises a plurality of amphiphilic molecules dispersed in an aqueous solution, said amphiphilic molecules comprising a hydrophilic component having at least a first and second terminus and at least a first and second hydrophobic moiety separately attached to, or proximal to, said first and second terminus of said hydrophilic component.

43. A composition comprising a liquid-crystalline multimolecular aggregate comprising a selected agent; wherein said liquid-crystalline multimolecular aggregate comprises a plurality of amphiphilic molecules dispersed in an aqueous solution, said amphiphilic molecules comprising a hydrophilic component having covalently attached, at spatially distant sites, at least two hydrophobic moieties, wherein the mesophases of said liquid-crystalline multimolecular aggregates, as characterized by X-ray diffraction, include the fluid $L_\alpha$, gel $L_\beta$, and hexagonal mesophases.

44. The composition of claim 23, wherein said selected agent is an oxygen carrier, haemoglobin, a red blood cell or a coagulant.

45. The composition of claim 24, wherein said selected agent is an antigen, an antibody, a cytokine or an anti-inflammatory agent.

* * * * *

UNITED STATES PATENT AND TRADEMARK OFFICE
CERTIFICATE OF CORRECTION

PATENT NO. : 6,699,499 B1
DATED : March 2, 2004
INVENTOR(S) : Rajindra Aneja

It is certified that error appears in the above-identified patent and that said Letters Patent is hereby corrected as shown below:

Column 46,
Line 21, delete "claim 3" and insert -- claim 1 -- therefor.

Signed and Sealed this

Sixth Day of July, 2004

JON W. DUDAS
*Acting Director of the United States Patent and Trademark Office*